United States Patent
Angelaud et al.

(10) Patent No.: US 9,303,043 B2
(45) Date of Patent: Apr. 5, 2016

(54) PROCESS FOR MAKING BENZOXAZEPIN COMPOUNDS

(71) Applicant: Genentech, Inc., South San Francisco, CA (US)

(72) Inventors: Remy Angelaud, San Francisco, CA (US); Danial R. Beaudry, San Mateo, CA (US); Diane E. Carrera, Belmont, CA (US); Sushant Malhotra, Burlingame, CA (US); Travis Remarchuk, San Francisco, CA (US); Frederic St-Jean, San Francisco, CA (US)

(73) Assignee: Greentech, Inc., South San Francisco, CA (US)

( * ) Notice: Subject to any disclaimer, the term of this patent is extended or adjusted under 35 U.S.C. 154(b) by 112 days.

(21) Appl. No.: 14/205,634

(22) Filed: Mar. 12, 2014

(65) Prior Publication Data
US 2014/0275523 A1    Sep. 18, 2014

Related U.S. Application Data

(60) Provisional application No. 61/779,619, filed on Mar. 13, 2013.

(51) Int. Cl.
| C07D 233/54 | (2006.01) |
| C07D 249/08 | (2006.01) |
| C07D 267/14 | (2006.01) |
| C07D 498/04 | (2006.01) |

(52) U.S. Cl.
CPC .................. C07D 498/04 (2013.01)

(58) Field of Classification Search
CPC .. C07D 233/54; C07D 249/08; C07D 267/14; C07D 498/04
USPC ......... 540/548, 552; 548/266.2, 266.8, 333.5, 548/334.5; 564/244
See application file for complete search history.

(56) References Cited

U.S. PATENT DOCUMENTS

| 7,928,248 B2 | 4/2011 | Do et al. |
| 8,242,104 B2 | 8/2012 | Blaquiere et al. |
| 8,263,633 B2 | 9/2012 | Blaquiere et al. |
| 8,343,955 B2 | 1/2013 | Blaquiere et al. |
| 8,586,574 B2 | 11/2013 | Blaquiere |
| 8,673,952 B2 | 3/2014 | Blaquiere |
| 8,785,626 B2 | 7/2014 | Blaquiere |
| 2012/0245144 A1 | 9/2012 | Heffron |
| 2014/0044706 A1 | 2/2014 | Belvin |

FOREIGN PATENT DOCUMENTS

| WO | 2008/088881 | 7/2008 |
| WO | 2009/150240 | 12/2009 |
| WO | 2011/036280 A1 | 3/2011 |

OTHER PUBLICATIONS

Ndubaku et al., "Discovery of 2-{3-[2-(1-Isopropyl-3-methyl-1H-1,2-4-triazol-5-y1)-5,6-dihydrobenzo[f]imidazo[1,2-d][1,4]oxazepin-9-yl]-1H-pyrazol-1-yl}-2-methylpropanamide (GDC-0032): A β-Sparing Phosphoinositide 3-Kinase Inhibitor with High Unbound Exposure and Robust in Vivo Antitumor Activity" J. Med. Chem.56:4597-4610 (2013).

Staben et al., "Cis-amide isosteric replacement in thienobenzoxepin inhibitors of PI3-kinase" Bioorg Med Chem Lett. 23(3):897-901 (2013).

Staben et al., "Discovery of thiazolobenzoxepni PI3-kinase inhibitors that spare the PI3-kinase β isoform" Bioorganic and Medicinal Chemistry Letters 23(9):2606-13 (May 1, 2013).

Staben et al., "Structure-based design of thienobenzoxepin inhibitors of PI3-kinase" Bioorg Med Chem Lett. 21:4054-8 (2011).

*Primary Examiner* — Brenda Coleman
(74) *Attorney, Agent, or Firm* — Alex Andrus

(57) ABSTRACT

Processes are described for the preparation of PI3K inhibitor, GDC-0032, Formula I, having the structure:

(GDC-0032)

and intermediates useful for the preparation of I.

10 Claims, No Drawings

PROCESS FOR MAKING BENZOXAZEPIN COMPOUNDS

CROSS REFERENCE TO RELATED APPLICATIONS

This non-provisional application filed under 37 CFR §1.53(b), claims the benefit under 35 USC §119(e) of U.S. Provisional Application Ser. No. 61/779,619 filed on 13 Mar. 2013, which is incorporated by reference in entirety.

FIELD OF THE INVENTION

The invention relates to methods of making a PI3K inhibitor compound GDC-0032

BACKGROUND OF THE INVENTION

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The main PI3-kinase isoform in cancer is the Class I PI3-kinase, p110α (alpha) (U.S. Pat. Nos. 5,824,492; 5,846,824; 6,274,327). Other isoforms are implicated in cardiovascular and immune-inflammatory disease (Workman P (2004) Biochem Soc Trans 32:393-396; Patel et al (2004) Proceedings of the American Association of Cancer Research (Abstract LB-247) 95th Annual Meeting, March 27-31, Orlando, Fla., USA; Ahmadi K and Waterfield M D (2004) Encyclopedia of Biological Chemistry (Lennarz W J, Lane M D eds) Elsevier/Academic Press). The PI3 kinase/Akt/PTEN pathway is an attractive target for cancer drug development since such modulating or inhibitory agents would be expected to inhibit proliferation, reverse the repression of apoptosis and surmount resistance to cytotoxic agents in cancer cells (Folkes et al (2008) J. Med. Chem. 51:5522-5532; Yaguchi et al (2006) Jour. of the Nat. Cancer Inst. 98(8):545-556). The PI3K-PTEN-AKT signaling pathway is deregulated in a wide variety of cancers (Samuels Y, Wang Z, Bardellil A et al. High frequency of mutations of the PIK3CA gene in human cancers. (2004) Science; 304 (5670):554; Carpten J, Faber A L, Horn C. "A transforming mutation in the pleckstrin homology domain of AKT1 in cancer" (2007) Nature; 448:439-444).

GDC-0032, also known as 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide, has potent PI3K activity (WO 2011/036280; U.S. Pat. No. 8,242,104) and is being studied in patients with locally advanced or metastatic solid tumors.

SUMMARY OF THE INVENTION

The invention relates to methods of making the PI3K inhibitor I (GDC-0032), named as 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide, having the structure:

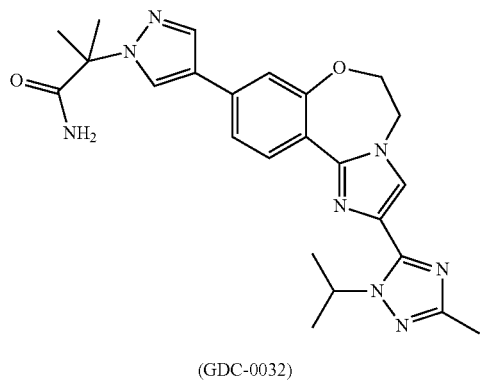

(GDC-0032)

and stereoisomers, geometric isomers, tautomers, and pharmaceutically acceptable salts thereof.

Another aspect of the invention includes novel intermediates useful for preparing GDC-0032 and having the structures:

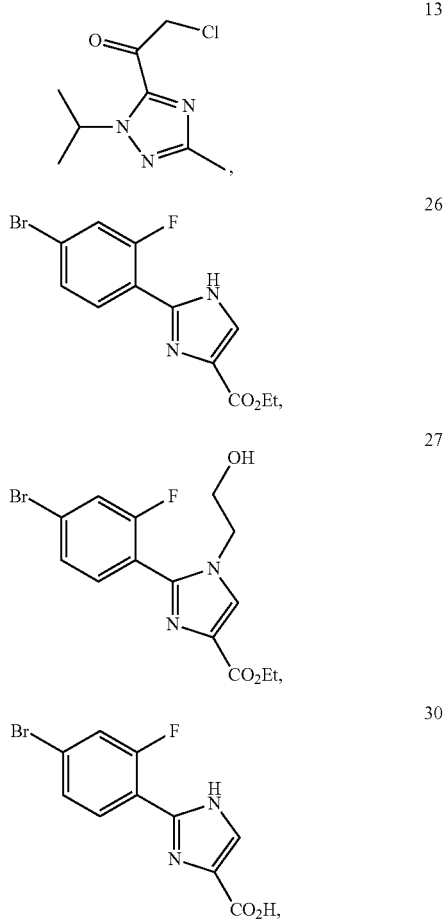

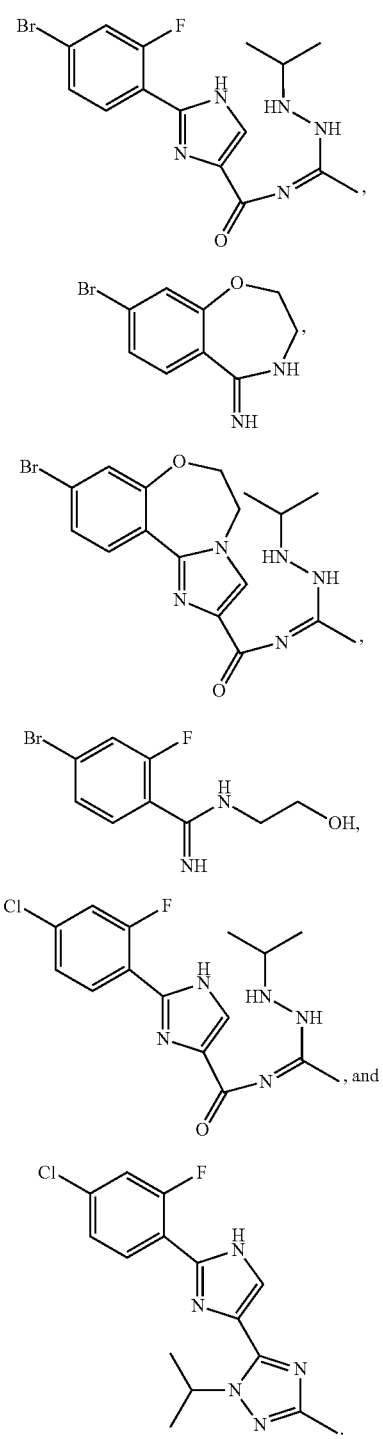

DEFINITIONS

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Preparation of GDC-0032

The present invention includes processes, methods, reagents, and intermediates for the synthesis of GDC-0032, Formula I, a small molecule inhibitor of PI3K and mTOR, (Roche RG7604, CAS Reg. No. 1282512-48-4), which has the structure:

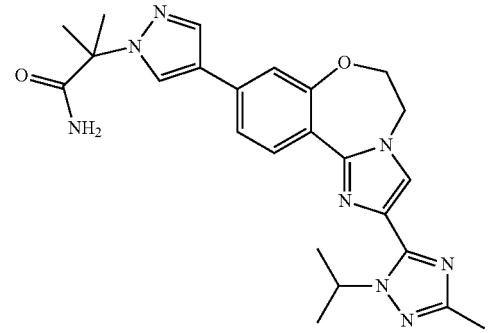

GDC-0032 and may be named: 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide (U.S. Pat. No. 8,242,104; WO 2011/036280 which are expressly incorporated by reference). As used herein, GDC-0032 includes all stereoisomers, geometric isomers, tautomers, and pharmaceutically acceptable salts thereof.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In addition, the present invention embraces all geometric and positional isomers. In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the invention may exist in unsolvated as well as solvated forms with pharmaceutically acceptable solvents such as water, ethanol, and the like, and it is intended that the invention embrace both solvated and unsolvated forms.

The compounds of the invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The compounds of the invention also include isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^3$H and $^{14}$C) are useful in compound and/or substrate tissue distribution assays. Tritiated ($^3$H) and carbon-14 ([4]C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

Starting materials and reagents for the preparation of GDC-0032 are generally available from commercial sources such as Sigma-Aldrich Chemical (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

The following Schemes 1-15 illustrate the chemical reactions, processes, methodology for the synthesis of GDC-0032, Formula I, and certain intermediates and reagents.

Scheme 1:

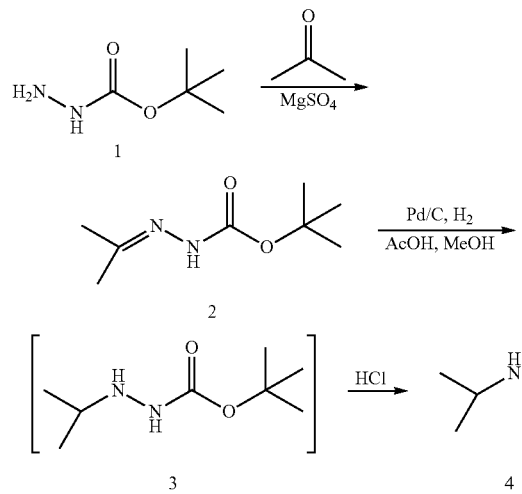

Scheme 1 shows the synthesis of intermediate isopropyl-hydrazine hydrochloride 4 from Boc-hydrazine 1. Condensation of 1 with acetone and magnesium sulfate gave Boc-hydrazone, tert-butyl 2-(propan-2-ylidene)hydrazinecarboxylate 2 (Example 1). Palladium-catalyzed hydrogenation of 2 in acetic acid and methanol gave Boc-isopropyl-hydrazine 3 (Example 2) which was treated in situ with hydrogen chloride gas to give 4 (Example 3).

Alternatively, the double bond of 2 can be reduced with a hydride reagent such as sodium cyanoborohydride (Example 2).

Scheme 2:

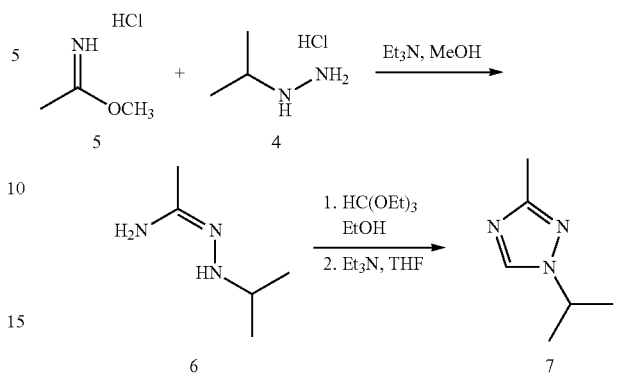

Scheme 2 shows the synthesis of 1-isopropyl-3-methyl-1H-1,2,4-triazole 7 from methyl acetimidate hydrochloride 5 and isopropylhydrazine hydrochloride 4. Reaction of 5 and 4 in triethylamine and methanol followed by cyclization of condensation product, N'-isopropylacetohydrazonamide 6 (Example 4) with triethyl orthoformate (triethoxymethane) gave 7 (Example 5). Alternatively, 4 and acetamidine can be reacted to give 6, or 4 can be reacted with acetonitrile and an acid to form the corresponding salt of 6.

Scheme 3:

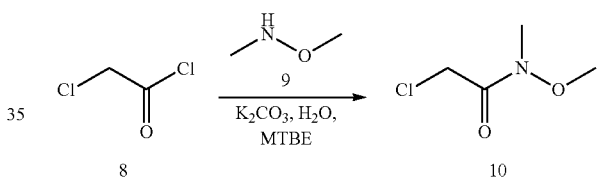

Scheme 3 shows the synthesis of intermediate, 2-chloro-N-methoxy-N-methylacetamide 10. Reaction of 2-chloro-acetyl chloride 8 and N,O-dimethylhydroxylamine hydrochloride 9 in aqueous potassium carbonate and methyl, tert-butyl ether (MTBE) gave 10 (Example 6).

Scheme 4:

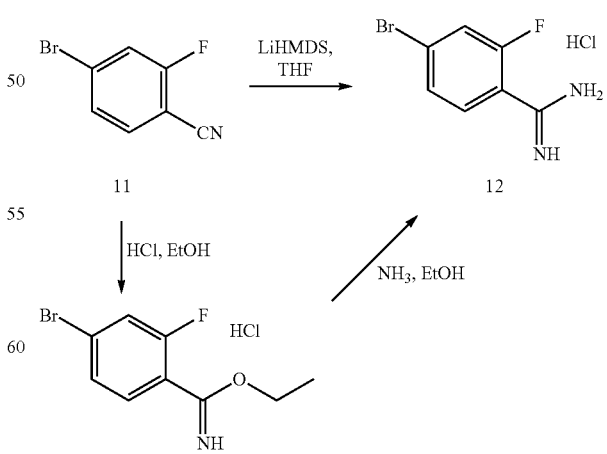

Scheme 4 shows the synthesis of intermediate 4-bromo-2-fluorobenzimidamide hydrochloride 12 formed by reaction of 4-bromo-2-fluorobenzonitrile 11 with lithium hexamethyldisilazide (LiHMDS) in tetrahydrofuran (Example 7). Alternatively, 11 is treated with hydrogen chloride in an alcohol, such as ethanol, to form the imidate, ethyl 4-bromo-2-fluorobenzimidate hydrochloride, followed by ammonia in an alcohol, such as ethanol, to form 12 (Example 7).

Scheme 5:

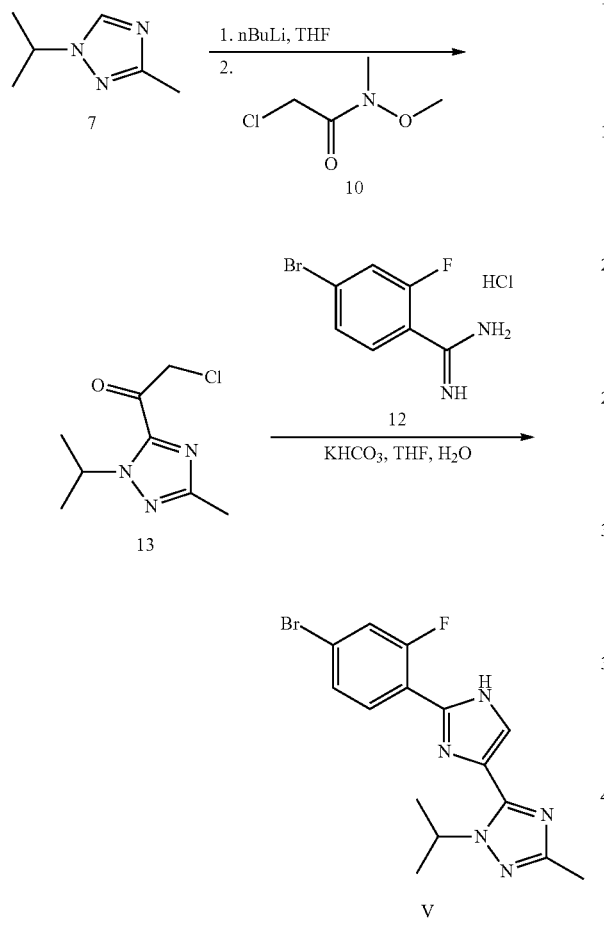

Scheme 5 shows the synthesis of 5-(2-(4-bromo-2-fluorophenyl)-1H-imidazol-4-yl)-1-isopropyl-3-methyl-1H-1,2,4-triazole V from 1-isopropyl-3-methyl-1H-1,2,4-triazole 7. Deprotonation of 7 with n-butyllithium and acylation with 2-chloro-N-methoxy-N-methylacetamide 10 gave intermediate 2-chloro-1-(1-isopropyl-3-methyl-1H-1,2,4-triazol-5-yl) ethanone 13 (Example 8). Cyclization of 13 with 4-bromo-2-fluorobenzimidamide hydrochloride 12 and potassium hydrogen carbonate in water and THF (tetrahydrofuran) formed the imidazole V (Example 9).

Scheme 6:

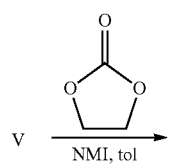

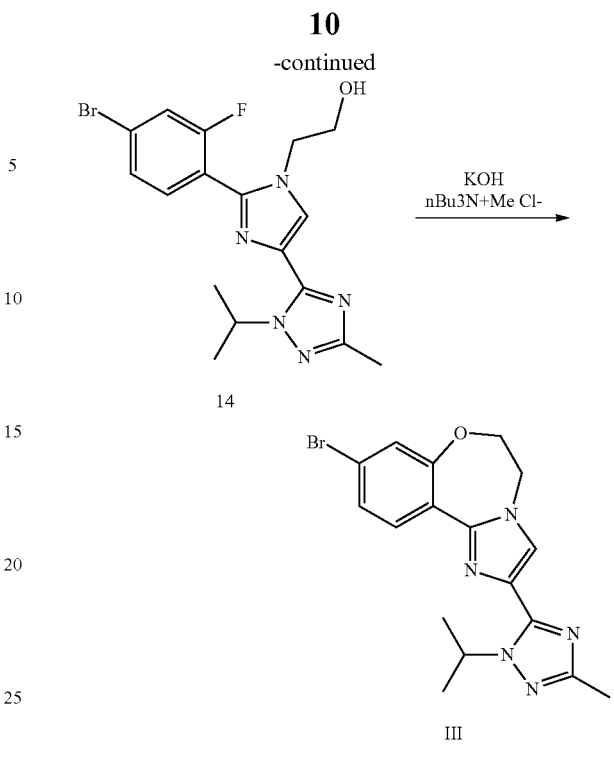

Scheme 6 shows the synthesis of 9-bromo-2-(1-isopropyl-3-methyl-1H-1,2,4-triazol-5-yl)-5,6-dihydrobenzo[f]imidazo[1,2-d][1,4]oxazepine III from V. Alkylation of the imidazole nitrogen of V with a 2-hydroxyethylation reagent such as, 1,3-dioxolan-2-one, gave 2-(2-(4-bromo-2-fluorophenyl)-4-(1-isopropyl-3-methyl-1H-1,2,4-triazol-5-yl)-1H-imidazol-1-yl)ethanol 14 (Example 10). Cyclization of 14 with an aqueous basic reagent, such as methyltributylammonium chloride in aqueous potassium hydroxide, gave III, which can be cystallized from ethanol and water (Example 11).

Scheme 7:

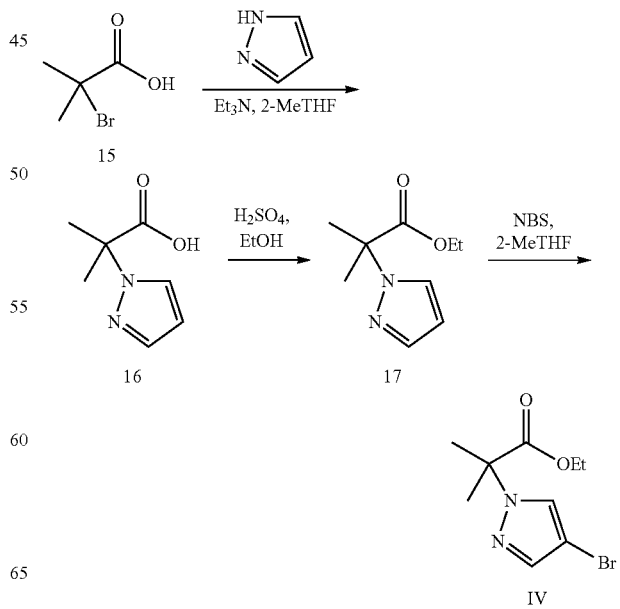

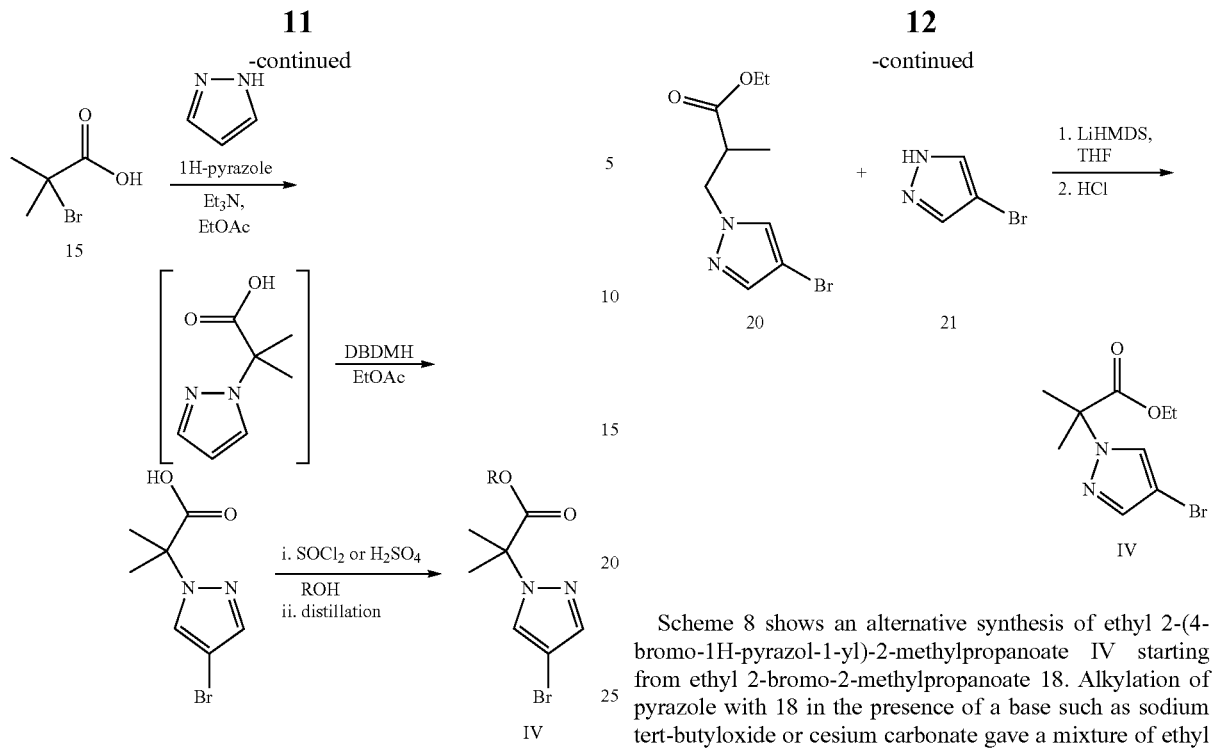

Scheme 7 shows the synthesis of ethyl 2-(4-bromo-1H-pyrazol-1-yl)-2-methylpropanoate IV starting from 2-bromo-2-methylpropanoic acid 15. Alkylation of pyrazole with 15 gave 2-methyl-2-(1H-pyrazol-1-yl)propanoic acid 16 (Example 12). Esterification of 16 with sulfuric acid in ethanol gave ethyl 2-methyl-2-(1H-pyrazol-1-yl)propanoate 17 (Example 13). Regiospecific bromination of 17 with N-bromosuccinimide (NBS) gave IV (Example 14). Alternatively, 16 was treated in situ with a brominating reagent such as 1,3-dibromo-5,5-dimethylhydantoin (DBDMH) to give 2-(4-bromo-1H-pyrazol-1-yl)-2-methylpropanoic acid which was esterified to give IV, where R is ethyl. Other esters can also be prepared, such as methyl, iso-propyl, or any alkyl, benzyl or aryl ester.

Scheme 8 shows an alternative synthesis of ethyl 2-(4-bromo-1H-pyrazol-1-yl)-2-methylpropanoate IV starting from ethyl 2-bromo-2-methylpropanoate 18. Alkylation of pyrazole with 18 in the presence of a base such as sodium tert-butyloxide or cesium carbonate gave a mixture of ethyl 2-methyl-2-(1H-pyrazol-1-yl)propanoate 17 and ethyl 2-methyl-3-(1H-pyrazol-1-yl)propanoate 19. Bromination of the mixture with 1,3-dibromo-5,5-dimethylimidazolidine-2,4-dione (DBDMH) gave a mixture containing IV, ethyl 3-(4-bromo-1H-pyrazol-1-yl)-2-methylpropanoate 20, and 4-bromo-1H-pyrazole 21 which was treated with a strong base under anhydrous conditions, such as lithium hexamethyldisilazide in tetrahydrofuran. Acidification with hydrochloric acid gave IV.

Scheme 9:

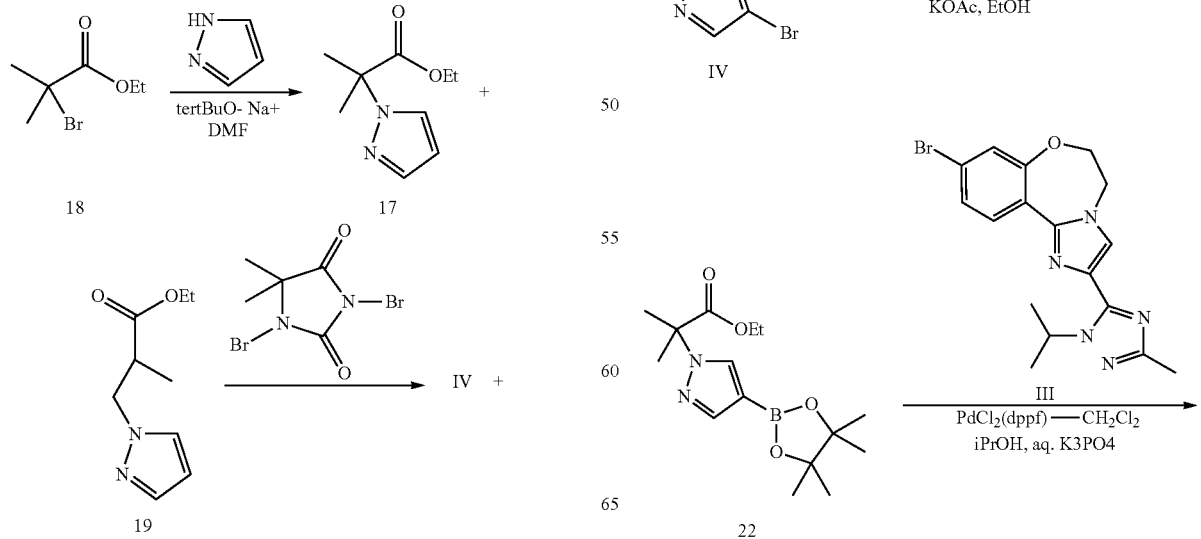

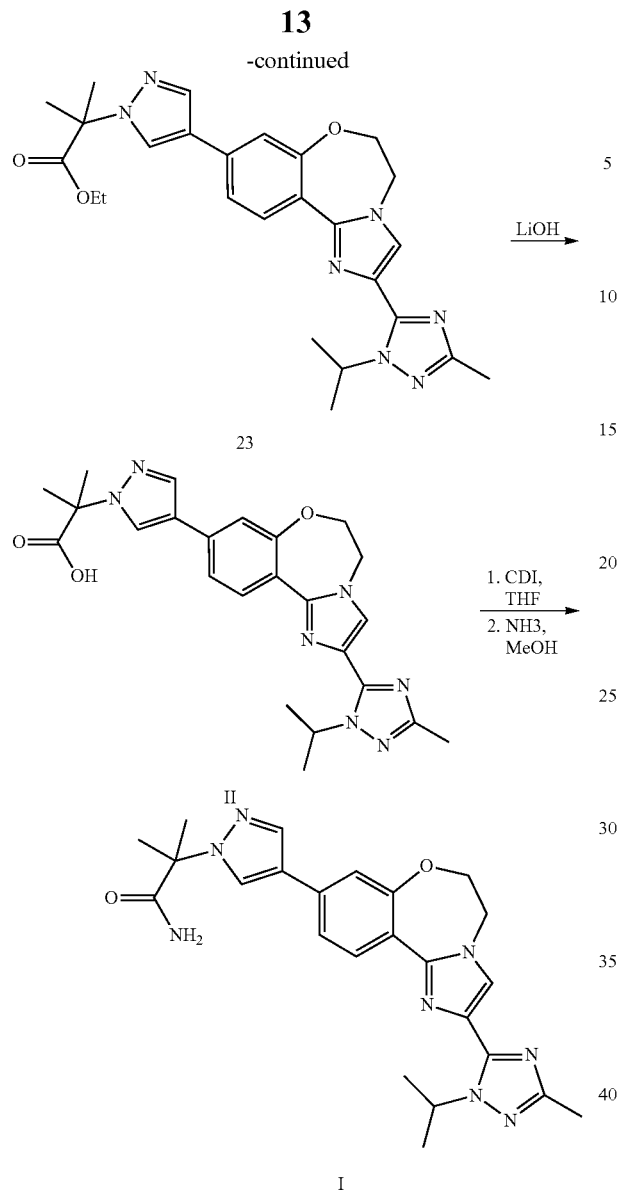

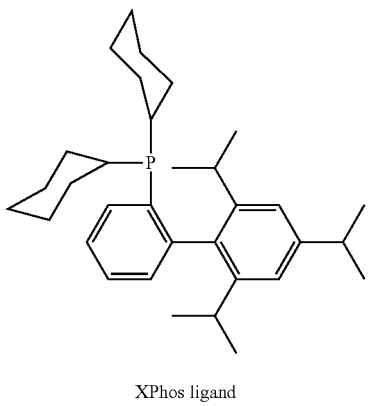 [SMILES: CC(C)c1cc(C(C)C)c(-c2ccccc2P(C2CCCCC2)C2CCCCC2)c(C(C)C)c1]

XPhos ligand 4,5,5-tetramethyl-1,3,2-dioxaborolan-2-yl)-1H-pyrazol-1-yl)propanoate 22 (Example 15, CAS Registry Number: 1201657-32-0, U.S. Pat. Nos. 8,242,104, 8,263,633, WO 2009/150240).

Intermediate 22 can be isolated or reacted in situ (one pot) with III to form 23.

A variety of low valent, Pd(II) and Pd(0) palladium catalysts can be used during the Suzuki coupling step to form 23 (Example 16) from 22 and III, including $PdCl_2(PPh_3)_2$, $Pd(t-Bu)_3$, $PdCl_2$ dppf $CH_2Cl_2$, $Pd(PPh_3)_4$, $Pd(OAc)/PPh_3$, $Cl_2Pd[(Pet_3)]_2$, $Pd(DIPHOS)_2$, $Cl_2Pd(Bipy)$, $[PdCl(Ph_2PCH_2PPh_2)]_2$, $Cl_2Pd[P(o-tol)_3]_2$, $Pd_2(dba)_3/P(o-tol)_3$, $Pd_2(dba)/P(furyl)_3$, $Cl_2Pd[P(furyl)_3]_2$, $Cl_2Pd(PMePh_2)_2$, $Cl_2Pd[P(4-F-Ph)_3]_2$, $Cl_2Pd[P(C_6F_6)_3]_2$, $Cl_2Pd[P(2-COOH-Ph)(Ph)_2]_2$, $Cl_2Pd[P(4-COOH-Ph)(Ph)_2]_2$, and encapsulated catalysts Pd EnCat™ 30, Pd EnCat™ TPP30, and Pd(II) EnCat™ BINAP30 (US 2004/0254066).

The ester group of 23 is saponified with an aqueous basic reagent such as lithium hydroxide, to give 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid II (Example 17). Intermediate 23 can be isolated or further reacted in situ with the aqueous basic reagent to form II. The carboxylic acid group of II is activated with an acyl activating reagent such as di(1H-imidazol-1-yl)methanone (carbonyl diimidazole, CDI) or N,N,N,N-tetramethyl-O-(7-azabenzotriazol-1-yl)uronium hexafluorophosphate (HATU), and then reacted with an alcoholic ammonia reagent, such as ammonia dissolved in methanol, ethanol, or isopropanol, aqueous ammonium hydroxide, aqueous ammonium chloride, or ammonia dissolved in THF, to give I (Example 18).

A variety of solid adsorbent palladium scavengers can be used to remove palladium after the Suzuki coupling step to form compound I. Exemplary embodiments of palladium scavengers include FLORISIL®, SILIABOND®Thiol, and SILIABOND® Thiourea. Other palladium scavengers include silica gel, controlled-pore glass (TosoHaas), and derivatized low crosslinked polystyrene QUADRAPURE™ AEA, QUADRAPURE™ IMDAZ, QUADRAPURE™ MPA, QUADRAPURE™ TU (Reaxa Ltd., Sigma-Aldrich Chemical Co.).

Scheme 9 shows the synthesis of 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide, GDC-0032, I from ethyl 2-(4-bromo-1H-pyrazol-1-yl)-2-methylpropanoate IV (CAS Registry Number: 1040377-17-0, WO 2008/088881) and 9-bromo-2-(1-isopropyl-3-methyl-1H-1,2,4-triazol-5-yl)-5,6-dihydrobenzo[f]imidazo[1,2-d][1,4]oxazepine III (CAS Registry Number: 1282514-63-9, US 2012/0245144, U.S. Pat. No. 8,242,104). Other esters besides ethyl can also be used which can be hydrolyzed with aqueous base, such as methyl, iso-propyl, or any alkyl, benzyl or aryl ester. In a one-pot Miyaura Borylation/Suzuki, Buchwald system, ethyl 2-(4-bromo-1H-pyrazol-1-yl)-2-methylpropanoate IV is reacted with 4,4,4',4',5,5,5',5'-octamethyl-2,2'-bi(1,3,2-dioxaborolane), CAS Reg. No. 73183-34-3, also referred to as $B_2Pin_2$, and a palladium catalyst such as XPhos (2-dicyclohexylphosphino-2',4',6'-triisopropylbiphenyl, CAS Reg. No. 564483-18-7), with a salt such as potassium acetate, in a solvent such as ethanol, at about 75° C. to form the intermediate ethyl 2-methyl-2-(4-(4, Scheme 10:

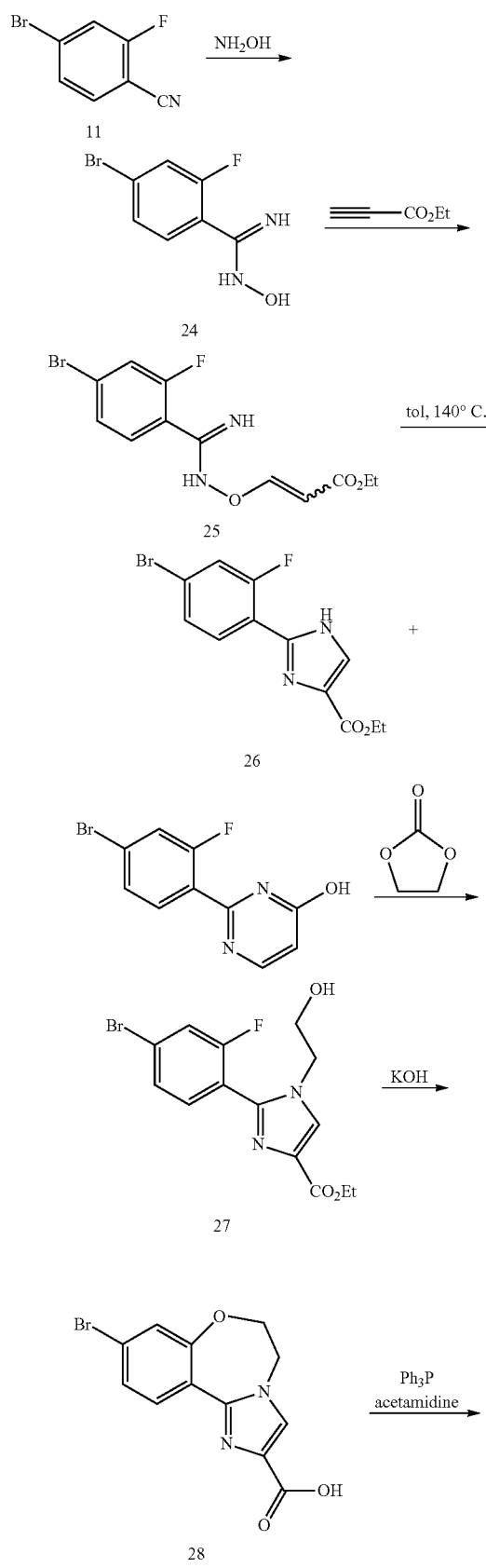

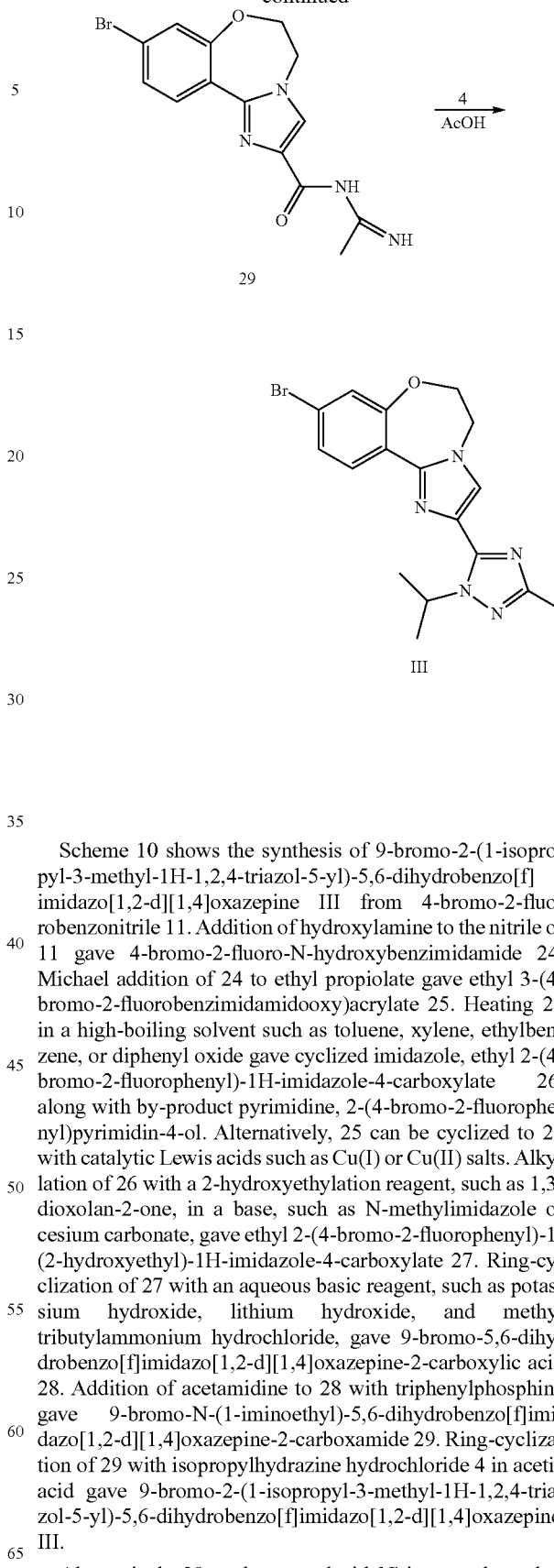

Scheme 10 shows the synthesis of 9-bromo-2-(1-isopropyl-3-methyl-1H-1,2,4-triazol-5-yl)-5,6-dihydrobenzo[f]imidazo[1,2-d][1,4]oxazepine III from 4-bromo-2-fluorobenzonitrile 11. Addition of hydroxylamine to the nitrile of 11 gave 4-bromo-2-fluoro-N-hydroxybenzimidamide 24. Michael addition of 24 to ethyl propiolate gave ethyl 3-(4-bromo-2-fluorobenzimidamidooxy)acrylate 25. Heating 25 in a high-boiling solvent such as toluene, xylene, ethylbenzene, or diphenyl oxide gave cyclized imidazole, ethyl 2-(4-bromo-2-fluorophenyl)-1H-imidazole-4-carboxylate 26, along with by-product pyrimidine, 2-(4-bromo-2-fluorophenyl)pyrimidin-4-ol. Alternatively, 25 can be cyclized to 26 with catalytic Lewis acids such as Cu(I) or Cu(II) salts. Alkylation of 26 with a 2-hydroxyethylation reagent, such as 1,3-dioxolan-2-one, in a base, such as N-methylimidazole or cesium carbonate, gave ethyl 2-(4-bromo-2-fluorophenyl)-1-(2-hydroxyethyl)-1H-imidazole-4-carboxylate 27. Ring-cyclization of 27 with an aqueous basic reagent, such as potassium hydroxide, lithium hydroxide, and methyl tributylammonium hydrochloride, gave 9-bromo-5,6-dihydrobenzo[f]imidazo[1,2-d][1,4]oxazepine-2-carboxylic acid 28. Addition of acetamidine to 28 with triphenylphosphine gave 9-bromo-N-(1-iminoethyl)-5,6-dihydrobenzo[f]imidazo[1,2-d][1,4]oxazepine-2-carboxamide 29. Ring-cyclization of 29 with isopropylhydrazine hydrochloride 4 in acetic acid gave 9-bromo-2-(1-isopropyl-3-methyl-1H-1,2,4-triazol-5-yl)-5,6-dihydrobenzo[f]imidazo[1,2-d][1,4]oxazepine III.

Alternatively, 28 can be reacted with N'-isopropylacetohydrazonamide 6 to give III (Scheme 12).

Scheme 11:

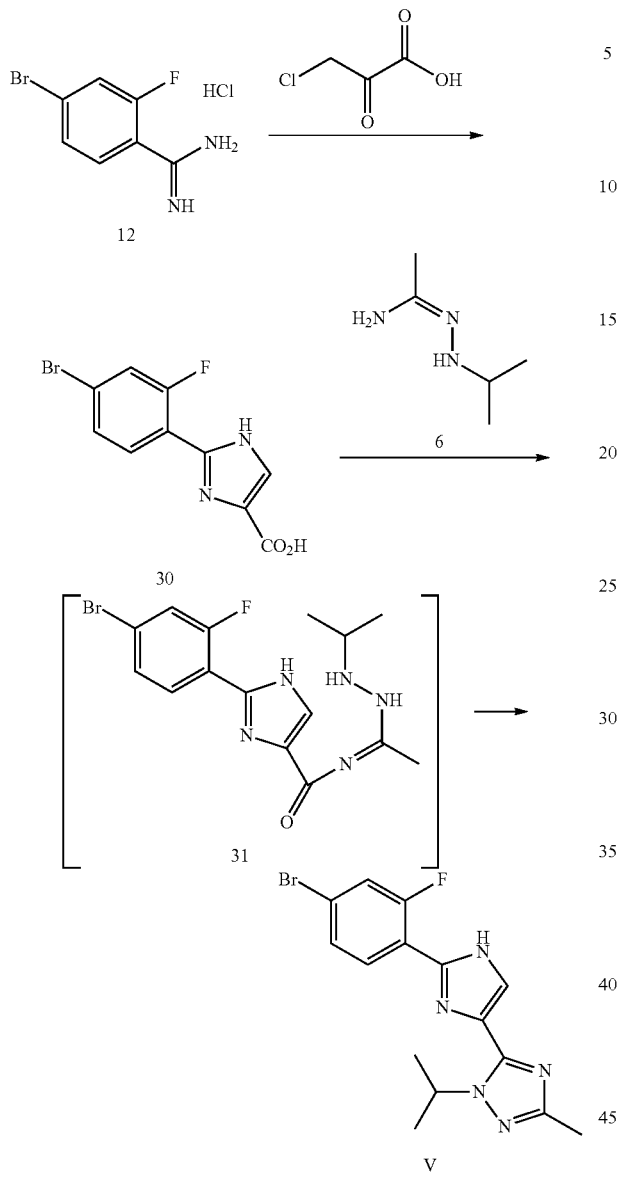

Scheme 12:

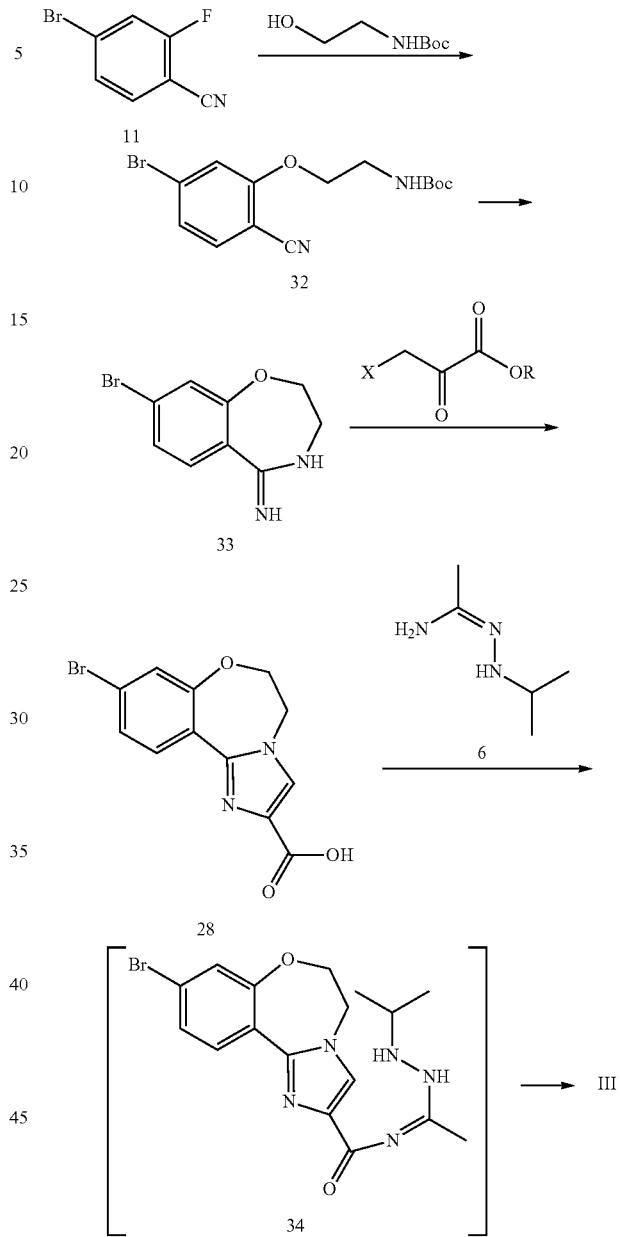

Scheme 11 shows the synthesis of 5-(2-(4-bromo-2-fluorophenyl)-1H-imidazol-4-yl)-1-isopropyl-3-methyl-1H-1,2,4-triazole V from 4-bromo-2-fluorobenzimidamide hydrochloride 12. 3-Chloro-2-oxopropanoic acid and 12 are reacted with base to give 2-(4-bromo-2-fluorophenyl)-1H-imidazole-4-carboxylic acid 30. Alternatively, 3-bromo-2-oxopropanoic acid can be reacted with 12 to give 30. Reaction of 30 with N'-isopropylacetohydrazonamide 6 and coupling reagent HBTU (N,N,N',N'-tetramethyl-O-(1H-benzotriazol-1-yl)uronium hexafluorophosphate, 0-(Benzotriazol-1-yl)-N,N,N',N'-tetramethyluronium hexafluorophosphate, CAS Ref No. 94790-37-1) in DMF gives intermediate, 2-(4-bromo-2-fluorophenyl)-N-(1-(2-isopropylhydrazinyl)ethylidene)-1H-imidazole-4-carboxamide 31 which need not be isolated and cyclizes upon heating to give V. Alternatively, 5-(2-(4-chloro-2-fluorophenyl)-1H-imidazol-4-yl)-1-isopropyl-3-methyl-1H-1,2,4-triazole 44, the chloro version of V, can be prepared from 4-chloro-2-fluorobenzonitrile 38 (Scheme 15)

Scheme 12 shows an alternative synthesis of 9-bromo-2-(1-isopropyl-3-methyl-1H-1,2,4-triazol-5-yl)-5,6-dihydrobenzo[f]imidazo[1,2-d][1,4]oxazepine III from 4-bromo-2-fluorobenzonitrile 11. Alkylation of 11 with tert-butyl 2-hydroxyethylcarbamate gives tert-butyl 2-(5-bromo-2-cyanophenoxy)ethylcarbamate 32. Cyclization of 32 under acidic conditions, such as hydrochloric acid in ethanol, gives 8-bromo-3,4-dihydrobenzo[f][1,4]oxazepin-5(2H)-imine 33. It will be noted that 33 has an alternative tautomeric form where the double bond is inside the oxazepine ring. Formation of the imidazole ring occurs by reaction of 3-bromo-2-oxopropanoic acid (X=Br, R=OH), or other 3-halo-2-oxopropanoic acid or ester (R=alkyl), and 33 to give 9-bromo-5,6-dihydrobenzo[f]imidazo[1,2-d][1,4]oxazepine-2-carboxylic acid 28. Coupling of 28 with N'-isopropylacetohydrazonamide 6 and a coupling reagent such as HBTU, HATU or CDI in DMF gives intermediate, 9-bromo-N-(1-(2-isopropylhydrazinyl)ethylidene)-5,6-dihydrobenzo[f]imidazo[1,2-d][1,4]oxazepine-2-carboxamide 34, which need not be isolated and forms 9-bromo-2-(1-isopropyl-3-methyl-1H-1,2,4-triazol-5-yl)-5,6-dihydrobenzo[f]imidazo[1,2-d][1,4]oxazepine III upon heating. Alternatively, N'-isopropylacetohydrazonamide 6 is used as the monohydrochloride salt, which has to be set free under the reaction conditions with an appropriate base, such as $K_2CO_3$.

Scheme 13:

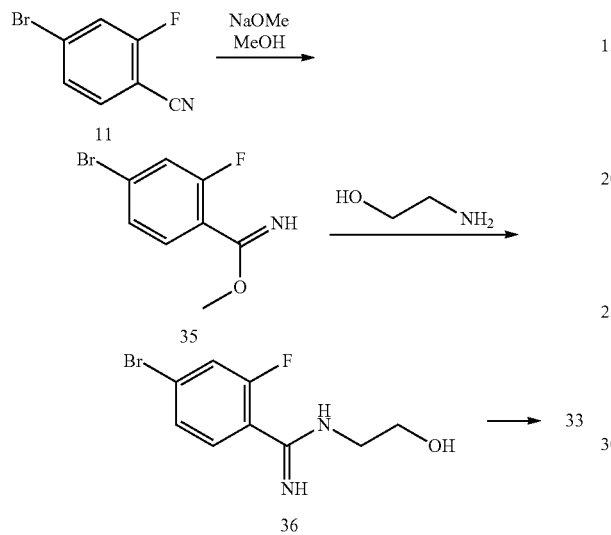

Scheme 13 shows an alternative synthesis of 8-bromo-3,4-dihydrobenzo[f][1,4]oxazepin-5(2H)-imine 33 from 4-bromo-2-fluorobenzonitrile 11. Reaction of 11 with sodium methoxide in methanol gives methyl 4-bromo-2-fluorobenzimidate 35. Alkylation of 35 with 2-aminoethanol gives 4-bromo-2-fluoro-N-(2-hydroxyethyl)benzimidamide 36, followed by cyclization to 33.

Scheme 14:

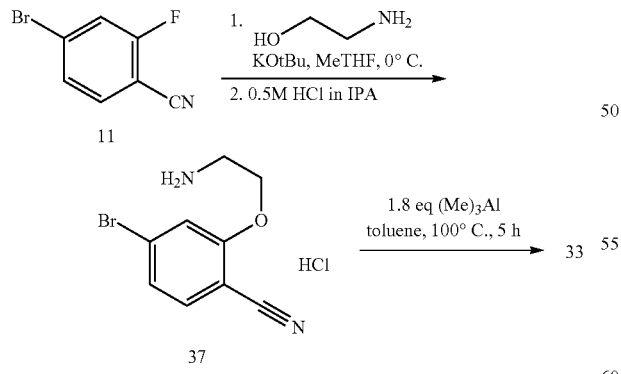

Scheme 14 shows another alternative synthesis of 8-bromo-3,4-dihydrobenzo[f][1,4]oxazepin-5(2H)-imine 33 from 4-bromo-2-fluorobenzonitrile 11. Reaction of 11 with 2-aminoethanol and potassium tert-butoxide displaces fluorine to give 2-(2-aminoethoxy)-4-bromobenzonitrile hydrochloride 37. Ring closure of 37 with trimethylaluminum gave 33. Alternatively, other trialkylaluminum reagents can be used, or magnesium alkoxide reagents such as magnesium ethoxide (magnesium bisethoxide, CAS Reg. No. 2414-98-4) to cyclize 37 to 33.

Scheme 15:

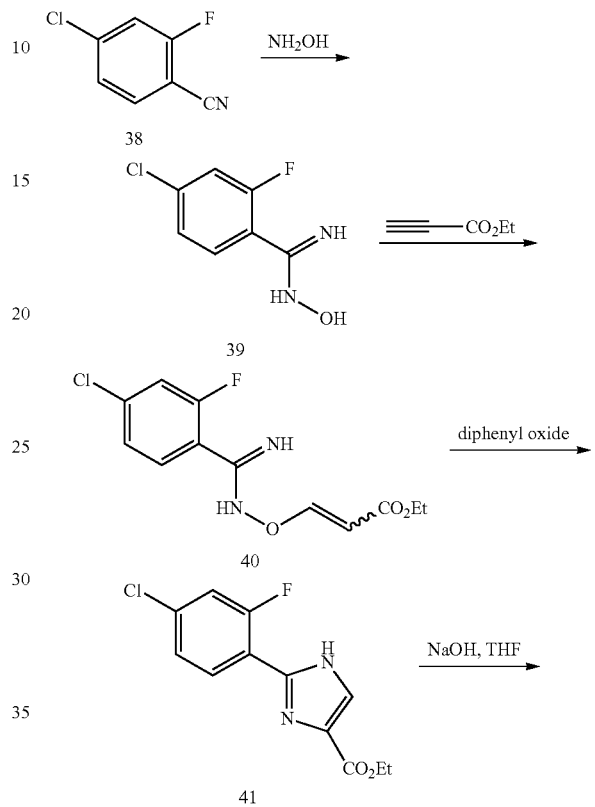

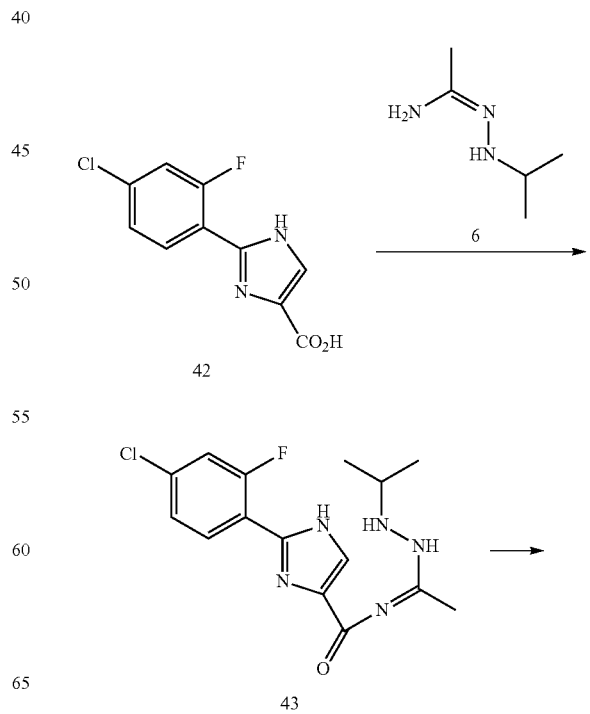

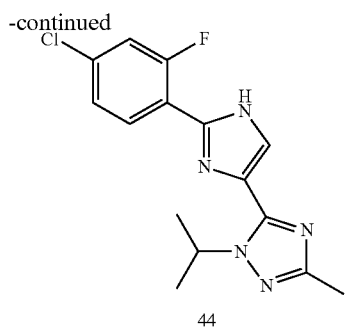

44

Scheme 15 shows the synthesis of 5-(2-(4-chloro-2-fluorophenyl)-1H-imidazol-4-yl)-1-isopropyl-3-methyl-1H-1,2,4-triazole 44 from 4-chloro-2-fluorobenzonitrile 38. Addition of hydroxylamine to the nitrile of 38 gave 4-chloro-2-fluoro-N-hydroxybenzimidamide 39. Michael addition of 39 to ethyl propiolate gave ethyl 3-(4-chloro-2-fluorobenzimidamidooxy)acrylate 40. Heating 40 in diphenyl oxide gave cyclized imidazole, ethyl 2-(4-chloro-2-fluorophenyl)-1H-imidazole-4-carboxylate 41. Saponification of the ester of 41 with aqueous sodium hydroxide in tetrahydrofuran gave 2-(4-chloro-2-fluorophenyl)-1H-imidazole-4-carboxylic acid 42. Reaction of 42 with N'-isopropylacetohydrazonamide 6 and coupling reagent HBTU in DMF gives intermediate, 2-(4-chloro-2-fluorophenyl)-N-(1-(2-isopropylhydrazinyl)ethylidene)-1H-imidazole-4-carboxamide 43 which cyclizes upon heating to give 44.

Formulations

GDC-0032, Formula I, may be formulated in accordance with standard pharmaceutical practice for use in a therapeutic combination for therapeutic treatment (including prophylactic treatment) of hyperproliferative disorders in mammals including humans. The invention provides a pharmaceutical composition comprising GDC-0032 in association with one or more pharmaceutically acceptable carrier, glidant, diluent, or excipient.

Suitable carriers, diluents, glidants, and excipients are well known to those skilled in the art and include materials such as carbohydrates, waxes, water soluble and/or swellable polymers, hydrophilic or hydrophobic materials, gelatin, oils, solvents, water and the like.

The formulations may be prepared using conventional dissolution and mixing procedures. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration with pharmaceutically acceptable diluents, carriers, excipients, glidants or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a tablet, a pill, a capsule, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, ethanol, or benzylalcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as lactose, sucrose, mannitol, trehalose or sorbitol; salt-forming counter-ions such as sodium; metal complexes (e.g., Zn-protein complexes); and/or non-ionic surfactants such as TWEEN™, including Tween 80, PLURONICS™ or polyethylene glycol (PEG), including PEG400. The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa. Other examples of drug formulations can be found in Liberman, H. A. and Lachman, L., Eds., Pharmaceutical Dosage Forms, Marcel Decker, Vol 3, $2^{nd}$ Ed., New York, N.Y.

Pharmaceutically acceptable glidants may be selected from silicon dioxide, powdered cellulose, microcrystalline cellulose, metallic stearates, sodium aluminosilicate, sodium benzoate, calcium carbonate, calcium silicate, corn starch, magnesium carbonate, asbestos free talc, stearowet C, starch, starch 1500, magnesium lauryl sulfate, magnesium oxide, and combinations thereof.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences 18th Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

EXAMPLES

Example 1 tert-butyl 2-(propan-2-ylidene)hydrazinecarboxylate 2

To a solution of tert-butyl hydrazinecarboxylate 1 (CAS Reg. No. 870-46-2) (25.1 g, 0.190 mol) in acetone (185 mL) was added the magnesium sulfate (6 g) and 12 drops acetic acid (Wu et al (2012) Jour. Med. Chem. 55(6):2724-2736; WO 2007/056170; Zawadzki et al (2003) Polish Jour. Chem. 77(3):315-319). The mixture was heated to reflux for 2.5 h and cooled to rt and filtered. The filtrate was concentrated to give tert-butyl 2-(propan-2-ylidene)hydrazinecarboxylate 2 (CAS Reg. No. 16689-34-2) as an off-white solid (32 g, 98%) (used in the next step without further purification). LC-MS [M+H]+=172.9, RT=2.11 min. 1H NMR 300 MHz (CDCl3) d 7.35 (br s, 1H, NH), 2.04 (s, 3H), 1.82 (s, 3H), 1.54 (s, 9H); 13C NMR 300 MHz (CDCl3) d 152.9, 149.7, 80.7, 28.1, 25.3, 15.9.

Example 2 tert-butyl 2-isopropylhydrazinecarboxylate 3 tert-Butyl 2-(propan-2-ylidene)hydrazinecarboxylate 2 was reduced with palladium catalyst on carbon with hydrogen gas in acetic acid and methanol to give tert-butyl 2-isopropylhydrazinecarboxylate 3 (CAS Reg. No. 16689-35-3).

Alternatively, tert-Butyl 2-(propan-2-ylidene)hydrazinecarboxylate 2 (0.51 g, 3.0 mmol) was dissolved in 20 mL of THF, treated with NaBH3CN (0.19 g, 3.0 mmol) and a few mg of bromocresol green, followed by a solution of p-toluenesulfonic acid (0.57 g, 3.0 mmol) in 1.5 mL of THF which was added dropwise over approximately 1 h to maintain the reaction pH between 3.5-5.0. After stirring at room temperature for an additional hour, the solvent was removed by rotary evaporation, and the residue was partitioned between EtOAc (30 mL) and brine. The organic phase was extracted with sat. NaHCO$_3$, 20 mL and brine, evaporated to a residue and dissolved in 10 mL of ethanol. The ethanolic solution was treated with 3.6 mL of 1M NaOH solution (3.6 mmol) and left to stir at rt for 30 min. The solvent was removed by rotary evaporation and the residue was taken up into ethyl acetate and extracted with water. The organic layer was evaporated under reduced pressure and the residue was purified by column chromatography using 5% MeOH in DCM as eluent to collect tert-butyl 2-isopropylhydrazinecarboxylate 3 (0.4 g, 77% yield): mp=47-49° C.; Rf=0.44 (5% MeOH in DCM); 1H NMR 300 MHz (CDCl3) d 6.03 (s, N—H, 1H), 3.92 (s, N—H, 1H), 3.14 (m, 1H), 1.46 (s, 9H), 1.02 (d, 6H, J=6 Hz); 13C NMR 300 MHz (CDCl3) d 157.2, 80.8, 51.2, 28.7, 21.0.

Example 3

Isopropylhydrazine hydrochloride 4 tert-butyl 2-isopropylhydrazinecarboxylate 3 was treated with hydrochloric acid to remove the Boc protecting group and give 4 (CAS Reg. No. 16726-41-3).

Example 4

N'-isopropylacetohydrazonamide 6

Methyl acetimidate hydrochloride 5 (CAS Reg. No. 14777-27-6), isopropylhydrazine hydrochloride 4, and triethylamine were reacted in methanol to give 6 (CAS Reg. No. 73479-06-8).

Example 5

1-isopropyl-3-methyl-1H-1,2,4-triazole 7

N'-isopropylacetohydrazonamide 6 was treated with triethylorthoformate in ethanol, followed by triethylamine and tetrahydrofuran to give 7 (CAS Reg. No. 1401305-30-3).

Example 6

2-chloro-N-methoxy-N-methylacetamide 10

To a solution of 21.2 kg) potassium carbonate K$_2$CO$_3$ (153.7 mol, 3.0 eq) in 30 L H$_2$O was added, N,O-dimethylhydroxylamine 9 (CAS Reg. No. 1117-97-1) (5.0 kg, 51.3 mol, 1.0 eq) at 15~20° C. The reaction was stirred at rt for 30 min and 30 L methyl tert-butyl ether (TBME) was added. After stirred for 30 min, the mixture was cooled to 5° C., and 11.6 kg of 2-Chloroacetyl chloride 8 (CAS Reg. No. 79-04-9 (102.7 mol, 2.0 eq) were added slowly. The reaction was stirred at rt overnight. Organics were separated from aqueous, and aqueous was extracted with TBME (30 L). The combined organics were washed with H$_2$O (50 L), brine (50 L) and dried over Na$_2$SO$_4$. Filtered and concentrated under vacuum afforded 5.1 kg of 2-chloro-N-methoxy-N-methylacetamide 10 (CAS Reg. No. 67442-07-3) as a white solid.

Example 7

4-bromo-2-fluorobenzimidamide hydrochloride 12

To 35.0 L of lithium hexamethyldisilazide LiHMDS (35.0 mol, 1.4 eq, 1.0 M in THF) under N$_2$ was added a THF solution of 4-Bromo-2-fluorobenzonitrile 11 (CAS Reg. No. 105942-08-3) (5.0 kg in 10 L THF) at 10° C., the mixture was stirred at rt for 3 h. Cooled to −20° C. and 8.3 L of HCl-EtOH (6.6 M) were added. The mixture was stirred at −10° C. for additional 1 h, filtered. The wet cake was washed with EA (10 L) and $H_2O$ (6 L). Drying in vacuo yielded 5.8 kg 4-bromo-2-fluorobenzimidamide hydrochloride 12 (CAS Reg. No. 1187927-25-8) as an off-white solid.

Alternatively, to a 200-L vessel was charged 4-bromo-2-fluorobenzonitrile 11 (10 kg, 50.00 mol, 1.00 equiv) and ethanol (100 L) followed by purging 40 kg Hydrogen chloride (g) at −10° C. with stirring (Scheme 4). The resulting solution was allowed to react for an additional 36 h at 10° C. The reaction progress was monitored by TLC until 11 was consumed completely. The resulting mixture was concentrated under vacuum while maintaining the temperature below 60° C. The volume was concentrated to 10~15 L before 60 L MTBE was added to precipitate the product. The precipitates were collected by filtration to afford in 12 k g of ethyl 4-bromo-2-fluorobenzimidate hydrochloride 12 as a white solid. (Yield: 85%). 1H NMR δ 7.88-7.67 (m), 4.89 (br s), 4.68 (q), 3.33 (m), 1.61 (t). MS M+1: 245.9, 248.0.

To a 200 L vessel, was charged ethyl 4-bromo-2-fluorobenzimidate hydrochloride (12.5 k g, 44 mol, 1.00 equiv, 99%) and ethanol (125 L) followed by purging $NH_3$ (g) at −5° C. for 12 h. The resulting solution was stirred at 30° C. for an additional 24 h. The reaction progress was monitored by TLC until SM was consumed completely. The precipitates were filtered and the filtrate was concentrated under vacuum. The product was precipitated and collected by filtration to afford 6.1 kg (54.5%) of 4-bromo-2-fluorobenzamidine hydrochloride 12 as a white solid. 1H NMR δ 9.60 (br), 7.91-7.64 (m), 3.40 (s), 2.50 (m). MS M+1: 216.9, 219.9.

Example 8

2-chloro-1-(1-isopropyl-3-methyl-1H-1,2,4-triazol-5-yl)ethanone 13

To a 10 L four necked flask was charged 1-Isopropyl-3-methyl-1H-1,2,4-triazole 7 (400 g) in THF (2.5 L). The resulting solution was cooled to −40° C. and 2.5 M n-butyllithium BuLi in n-hexanes (1.41 L) was added while keeping the internal temp. below −20° C. The resulting yellow suspension was stirred at −40° C. for 1 hour before being transferred. To a 20 L flask was charged 2-chloro-N-methoxy-N-methylacetamide 10 (485 g) in THF (4 L). The resulting solution was cooled to −40° C. at which point a white suspension was obtained, and to this was added the solution of lithiated triazole 7 keeping the internal temp. below −20° C. At this point a yellow orange solution was obtained which was stirred at −30° C. for 1 hour. Propionic acid (520 mL) was added keeping the internal temp. below −20° C. The resulting off-white to yellowish suspension was warmed to −5° C. over 30 minutes. Citric acid (200 g) in water (0.8 L) was added and after stirring for 5 minutes a clear biphasic mixture was obtained. At this point stirring was stopped and the bottom aqueous layer was removed. The organic phase was washed with 20 w % $K_3PO_4$ solution (1 L), 20 w % $K_2HPO_4$ solution (2 L), and 20 w % NaCl solution (1 L). The organics was reduced to ca 4 L via distillation under vacuum to afford 2-chloro-1-(1-isopropyl-3-methyl-1H-1,2,4-triazol-5-yl) ethanone 13 as a dark amber liquid which was used "as is" in the next step.

Example 9

5-(2-(4-bromo-2-fluorophenyl)-1H-imidazol-4-yl)-1-isopropyl-3-methyl-1H-1,2,4-triazole V To a 10 L four-neck flask were charged with THF (5.6 L), 4-bromo-2-fluorobenzimidamide hydrochloride 12 (567 g), $KHCO_3$ (567 g) and water (1.15 L). The resulting white suspension was heated to 60° C. over 2 hours. At this point a hazy solution was obtained to which was added a solution of 2-Chloro-1-(1-isopropyl-3-methyl-1H-1,2,4-triazol-5-yl) ethanone 13 in THF (2 L). This solution was stirred at 60-65° C. for 24 hours. Then the aqueous bottom layer was removed. The organic layer was concentrated under vacuum. The residue was slurried in a mixture of MIBK (1.25 L) and toluene (0.7 L), and the precipitated product was filtered giving 552 g of 5-(2-(4-bromo-2-fluorophenyl)-1H-imidazol-4-yl)-1-isopropyl-3-methyl-1H-1,2,4-triazole V (98.0% purity, 254 nm) as a brown solid Example 10

2-(2-(4-bromo-2-fluorophenyl)-4-(1-isopropyl-3-methyl-1H-1,2,4-triazol-5-yl)-1H-imidazol-1-yl) ethanol 14

5-(2-(4-Bromo-2-fluorophenyl)-1H-imidazol-4-yl)-1-isopropyl-3-methyl-1H-1,2,4-triazole V (2.75 kg, 7.55 mol) was added to a solution of 3-dioxolan-2-one (ethylene carbonate, 3.99 kg, 45.3 mol) in N-methylimidazole (12 L) at 50° C. The suspension was heated at 80° C. for 7 h until the reaction was judged complete by HPLC. The solution of 14 was cooled to 35° C. and used directly in the subsequent cyclization.

Example 11

9-bromo-2-(1-isopropyl-3-methyl-1H-1,2,4-triazol-5-yl)-5,6-dihydrobenzo[f]imidazo[1,2-d][1,4]oxazepine III To a solution of 2-(2-(4-Bromo-2-fluorophenyl)-4-(1-isopropyl-3-methyl-1H-1,2,4-triazol-5-yl)-1H-imidazol-1-yl) ethanol (7.55 mmol) 14 in N-methylimidazole(12 L) at 35° C. was added methyl tributylammonium chloride (115 g, 0.453 mol), toluene (27.5 L) and 35% potassium hydroxide solution (10.6 kg, 25 mol in 22 L of water). The biphasic solution was stirred vigorously at 65° C. for 18 h when it was judged complete by HPLC. Stirring was stopped but heating was continued and the bottom aqueous layer was removed. Added isopropyl acetate (13.8 L) and the organic phase was washed twice with water (13.8 L and 27.5 L). The solvent was removed via vacuum distillation and after 30 L had been removed, isopropanol (67.6 L) was added. Vacuum distillation was resumed until an additional 30 L of solvent had been removed. Added additional isopropanol (28.8 L) and continued vacuum distillation until the volume was reduced by 42 L. Added isopropanol (4 L) and the temperature was increased to >50° C. Added water (28 L) such that the internal temperature was maintained above 50° C., then heated to 75° C. to obtain a clear solution. The mixture was allowed to cool slowly and the product crystallized out of solution. The resulting suspension was cooled to 0° C., held for 1 h then filtered and the cake was washed with water (5.5 L). The cake was dried at 45° C. under a nitrogen sweep to give III as a tan solid (3.30 kg, 71.6 wt %, 80.6% yield).

Example 12

2-methyl-2-(1H-pyrazol-1-yl)propanoic acid 16

2-Bromo-2-methylpropanoic acid 15 and pyrazole were reacted in triethylamine and 2-methyltetrahydrofuran to give 16.

Example 13

Ethyl 2-methyl-2-(1H-pyrazol-1-yl)propanoate 17

2-Methyl-2-(1H-pyrazol-1-yl)propanoic acid 16 was treated with sulfuric acid in ethanol to give 17.

Alternatively, pyrazole (10 g, 147 mmol, 1.0 eq.) was dissolved in DMF (500 ml) at room temperature (Scheme 8). 2-Bromoisobutyrate 18 (22 ml, 147 mmol, 1.0 eq.), cesium carbonate $Cs_2CO_3$ (53 g, 162 mmol, 1.1 eq) and catalytic sodium iodide NaI (2.2 g, 15 mmol, 0.1, eq) were added to the mixture that was then heated to 60° C. for 24 hr. Reaction was followed by 1H NMR and pyrazole was not detected after 24 hr. The reaction mixture was quenched with a saturated solution of $NaHCO_3$ (200 ml) and ethyl acetate EtOAc (150 ml) was added and organics were separated from aqueous. Organics were dried over $Na_2SO_4$, filtered and concentrated under vacuum to afford an oil which was purified by flash chromatography to give 17.

Example 14

Ethyl 2-(4-bromo-1H-pyrazol-1-yl)-2-methylpropanoate IV

Method A: Ethyl 2-methyl-2-(1H-pyrazol-1-yl)propanoate 17 was reacted with N-bromosuccinimide (NBS) in 2-methyltetrahydrofuran to give IV (CAS Reg. No. 1040377-17-0).

Method B: Ethyl 2-bromo-2-methylpropanoate 18 and pyrazole were reacted with sodium tert-butoxide in dimethylformamide (DMF) to give a mixture of ethyl 2-methyl-2-(1H-pyrazol-1-yl)propanoate 17 and ethyl 2-methyl-3-(1H-pyrazol-1-yl)propanoate 19 which was treated with 1,3-dibromo-5,5-dimethylimidazolidine-2,4-dione to give a mixture of IV, ethyl 3-(4-bromo-1H-pyrazol-1-yl)-2-methylpropanoate 20, and 4-bromo-1H-pyrazole 21. The mixture was treated with a catalytic amount of lithium hexamethyldisilazide in tetrahydrofuran followed by acidification with hydrochloric acid to give IV.

Example 15

Ethyl 2-methyl-2-(4-(4,4,5,5-tetramethyl-1,3,2-dioxaborolan-2-yl)-1H-pyrazol-1-yl)propanoate 22

To a 50 L glass reactor was charged ethyl 2-(4-bromo-1H-pyrazol-1-yl)-2-methylpropanoate IV (1.00 kg, 3.85 mol, 1.00 equiv), potassium acetate, KOAc (0.47 kg, 4.79 mol 1.25 equiv), 4,4,4',4',5,5,5',5'-octamethyl-2,2'-bi(1,3,2-dioxaborolane), bis(pinacolato)diboron, $B_2Pin_2$ (1.22 kg, 4.79 mol, 1.25 equiv) and ethanol (10 L, 10 vol) and the mixture was stirred until a clear solution was obtained. The solution was vacuum/degassed 3× with nitrogen. To this mixture was charged XPhos ligand (0.023 kg, 0.048 mol, 1.0 mol %) and the Pd precatalyst (0.018 kg, 0.022 mol, 0.5 mol %) resulting in a homogeneous orange solution. The solution was vacuum/degassed once with nitrogen. The internal temperature of the reaction was set to 75° C. and the reaction was sampled every 30 min once the set temperature was reached and was monitored by LC (IPC method: XTerra MS Boronic). After 5 h, conversion to 22 (CAS Reg. No. 1201657-32-0) was almost complete, with 1.3% IV remaining

Example 16

Ethyl 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate 23

Ethyl 2-methyl-2-(4-(4,4,5,5-tetramethyl-1,3,2-dioxaborolan-2-yl)-1H-pyrazol-1-yl)propanoate 22 and 9-bromo-2-(1-isopropyl-3-methyl-1H-1,2,4-triazol-5-yl)-5,6-dihydrobenzo[f]imidazo[1,2-d][1,4]oxazepine III were reacted under Suzuki conditions with palladium catalyst, in isopropanol and aqueous phosphate buffer to give 23.

A 1M solution of $K_3PO_4$ (1.60 kg in 7.6 L of water, 7.54 mol, 2.00 equiv) was charged to the above reaction mixture from Example 15, followed by the addition of a solution of III in THF (1.33 kg in 5.0 L, 3.43 mol, 0.90 equiv) over 2 min. The reaction mixture was warmed to 75° C. (internal temperature) over 45 min and stirred for 13 h at 75° C., then analyzed by HPLC (III not detected) showing the formation of 23.

Example 17

2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid II Ethyl 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate 23 was treated with aqueous lithium hydroxide to give II.

The ester saponification reaction was initiated with the addition of 3.5 M aqueous LiOH (0.74 kg in 5.0 L, 17.64 mol, 5 equiv) to the reaction mixture from Example 16 and allowed to warm to 75° C. The mixture was sampled every 30 min (IPC method: XTerra MS Boronic) and the saponification was complete after 4.5 h (with less than 0.3% 23 remaining) The reaction mixture was concentrated via distillation to approximately half volume (starting vol=37 L; final vol=19 L) to remove EtOH and THF, resulting in tan-brown slurry. Water (5 L, 5 vol) was charged to the mixture and then distilled (starting vol=25 L; final vol=21 L). The temperature was set at 60° C. (jacket control) and then charged with isopropyl acetate, IPAc (4 L, 4 vol). The biphasic mixture was stirred a minimum of 5 min and then the layers allowed to separate for a minimum of 5 min. The bottom aqueous layer was removed into a clean carboy and the organics were collected into a second carboy. The extraction process was repeated a total of four times, until the organic layer was visibly clear. The aqueous mixture was transferred back to the reactor and then cooled to 15° C. A 6 M solution of HCl (6.4 L, 38.40 mol, 10 equiv) was charged slowly until a final pH=1 was obtained. The heterogeneous mixture was then filtered. The resulting solids were washed twice with 5 L (2×5 vol) of water. The filter was then heated to 80° C. and the vacuum set to −10 Psi (with nitrogen bleed) and the solids were dried for 24 h (KF=2.0% $H_2O$) to give 1.54 kg (95% corrected yield) of II as a white solid; 98% wt, 97.3% pure.

Example 18

2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide I (GDC-0032)

2-(4-(2-(1-Isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid II was treated with di(1H-imidazol-1-yl)methanone (carbonyldiimidazole, CDI) in tetrahydrofuran followed by methanolic ammonia to give crude I.

Solid II (1.44 kg, 3.12 mol, 1.00 equiv) was transferred into a 20 L bottle and then THF (10 L, 7 vol) was charged. The slurry was transferred under reduced pressure into a second 50 L reactor and additional THF (5 L, 3 vol) was added for the rinse. The internal temperature of the slurry was set to 22° C. and 1'1-carbonyldiimidazole, CDI (0.76 Kg, 5.12 mol, 1.50 equiv) was charged to the mixture and a clear solution was observed after 5 min. The reaction mixture was sampled every 30 min and analyzed by HPLC (IPC: XTerra MS Boronic method) which showed almost complete conversion to the acyl-imidazole intermediate and 1.2% remaining II after 30 min. An additional portion of CDI (0.07 kg, 0.15 mol, 0.14 equiv) was added, and the reaction mixture was stirred for 1 h and then analyzed by HPLC (IPC: XTerra MS Boronic method) which showed 0.8% remaining II.

Into a second 50-L reactor, was added $NH_3$/MeOH (1.5 L, 10.5 mol, 3.37 equiv) and THF (5 L, 3 vol). The acyl-imidazole intermediate was transferred to a second reactor under reduced pressure (transfer time ~10 min). The internal temperature was then set to 45° C. and the volume of solvent was distilled down from 35 L to 12 L. Water (6 L, 4 vol) was then added to the mixture that was further distilled from 18 L to 11 L. Finally, another portion of water (6 L, 4 vol) was added and the solvents were distilled one last time from 17 L to 14 L, until no more THF was coming out. The reaction was then cooled down to 10° C. (internal temperature). The white slurry was filtered and the filter cake was washed with water (2×6 L, 2×4 vol). The solids were then dried at 80° C. (jacket temp) in the Aurora filter for 24 h (KF=1.5% $H_2O$) under vacuum to give 1.25 kg crude I, GDC-0032 (84% corrected yield, 96% wt, 97.3% pure by HPLC) as a white solid.

A slurry of crude I (1.15 kg, 2.50 moles) in MeOH (6 L, 5 vol) was prepared and then charged to a 50 L glass reactor. Additional MeOH (24 L, 21 vol) was added to the mixture, which was then heated to 65° C. A homogenous mixture was obtained. Si-thiol (Silicycle, Inc., 0.23 kg, 20% wt) was added to the solution via the addition port and the mixture was stirred for 3 hours. It was then filtered warm via the Aurora filter (jacket temperature=60° C., polish filtered and transferred directly into a second 50 L reactor with reduced pressure. The solution was then heated back to 65° C. internal temperature (IT). The homogeneous solution was cooled down to 54° C. and I seeds (12 g, 1% wt) in MeOH (50 mL) were added with reduced pressure applied to the reactor. The mixture was then cooled down to 20° C. over 16 hours. The solids were then filtered via the Aurora filter and dried at 80° C. for 72 hours to give 921 g, 80% yield of I as a methanoate solvate (form A by XRPD) and transferred to a pre-weighed charge-point bag.

In an isolator, the solids were slurred in IPAc (8 L, 7 vol) and transferred to a clean 10 L reactor. The mixture was stirred for 1 h at 60° C. (IT). The solids were then filtered via the Aurora system and dried at 80° C. (jacket) for 96 h. A sample of I was removed and analyzed by GC (IPAc=1%). To attempt more efficient drying, the API was transferred to two glass trays in an isolator and sealed with a drying bag before being dried in a vacuum oven set at 100° C. for 16 h. GC (IPC: Q12690V2) showed 1% solvent was still present. The process afforded 760 g (68% corrected yield, 68% wt, 99.9% purity by LC) of a white solid (form B by XRPD)

Crude I (340.7 g) was charged to a 2-L HDPE bottle and slurried with 0.8 L isoamylalcohol OA). The slurry was transferred to a 20 L reactor and diluted with 6.7 round-bottom flask (22 vol total). The white slurry was heated until a solution was observed (internal temperature rose to 118° C. and then cooled to 109° C.). The solution was polish filtered (0.2 µM filter). A flask was equipped with overhead stirring and the filtrate was slurried in isoamyl alcohol (344 mL, 21 vol). The mixture was warmed to 95° C. (internal) until the solids dissolved. A slurry of charcoal (10 wt %, 0.16 g) and silicycle thiol (10 wt %, 0.16 g) in isoamyl alcohol (1 vol, 16 mL) was charged and the mixture was stirred at 90-95° C. for 1 h and then filtered (over Celite® pad). The clear amber colored solution was cooled to 73° C. (seeding temp range=70±5° C.) and a GDC-0032 I seed (10 wt %, 0.16 g) was added. The temperature of the heating mantle was turned off and the mixture was allowed to cool to room temperature overnight with stirring (200 rpm). After 17 hr, the white solids were filtered starting with slow gravity filtration and then vacuum was applied. The solids were suction dried for 20 min with mixing until a free flowing powder was obtained. Crude weight prior to oven drying=16 g. The solids were oven-dried at 100° C. for 24 h and then sampled for testing. Drying continued at 100° C. for another 24 hr. 1H NMR (DMSO d6) δ 8.38 (t), 8.01 (s), 7.87 (s), 7.44, 7.46 (d), 7.36 (s), 7.18 (br s), 6.81 (br s), 5.82 (m), 3.99 (s), 2.50 (s), 2.26 (s), 1.75 (s), 1.48, 1.46 (d).

Purified 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide I (GDC-0032) was dry granulation formulated in tablet form by the roller compaction method (He et al (2007) Jour. of Pharm. Sci., 96(5):1342-1355) with excipients including lactose, microcrystalline cellulose (AVICEL® PH 01, FMC BioPolymer, 50 µM particle), croscarmellose sodium (Ac-Di-Sol®, FMC BioPolymer), and magnesium stearate.

Example 19

4-bromo-2-fluoro-N-hydroxybenzimidamide 24

To a solution of 4-Bromo-2-fluorobenzonitrile 11 (800 g, 4 mol, 1 eq), hydroxylamine hydrochloride (695 g, 10 mol, 2.5 eq) in MeOH (2 L, 2.5 vol) was added Et3N (485 g, 4.8 mol, 1.2 eq), then the mixture was stirred at 60° C. for 40 min and checked by HPLC (no nitrile remaining) Reaction was then quenched by $H_2O$ (30 L), and lots of off-white solid was separated out, and then filtered, the filter cake was washed with water (10 L×2) and 1350 g wet 4-bromo-2-fluoro-N-hydroxybenzimidamide 24 was obtained with 96% purity

Example 20

Ethyl 3-(4-bromo-2-fluorobenzimidamidooxy)acrylate 25

To a solution of 4-Bromo-2-fluoro-N-hydroxybenzimidamide 24 (800 g, 3.43 mol, 1 eq) and Amberlyst® A21 (20 wt %, 160 g) in PhMe (12 L, 15 vol) was added ethyl propiolate (471 g, 4.8 mol, 1.4 eq) at 10° C. The reaction was stirred at 50° C. overnight and checked by LC-MS (ca 14A % of starting material 24 was left). Reaction was then filtered and the filtrate was concentrated under vacuum, and 1015 g ethyl 3-(4-bromo-2-fluorobenzimidamidooxy)acrylate 25 was obtained as a yellow oil with 84.9% LC purity (yield: 89%).

Example 21

Ethyl 2-(4-bromo-2-fluorophenyl)-1H-imidazole-4-carboxylate 26

A solution of ethyl 3-(4-bromo-2-fluorobenzimidamidooxy)acrylate 25 (300 g, 0.91 mol, 1 eq) in diphenyl oxide (900 mL, 3 vol) was stirred at 190° C. under N2 for 1 h and checked by LC-MS (no 25 remaining) Cooled the mixture to rt and TBME (600 mL, 2 vol of 25) was added, and then PE (1.8 L, 6 vol of 25) was dropwise added to separate out solids. The mixture was stirred at rt for 20 min, and filtered to give 160 g wet cake. The wet cake was washed with PE (1 L) and dried to afford 120 g ethyl 2-(4-bromo-2-fluorophenyl)-1H-imidazole-4-carboxylate 26 with 92% LC purity as brown solids.

Example 22

Ethyl 2-(4-bromo-2-fluorophenyl)-1-(2-hydroxyethyl)-1H-imidazole-4-carboxylate 27

Ethyl 2-(4-bromo-2-fluorophenyl)-1H-imidazole-4-carboxylate 26 and 1,3-dioxolan-2-one and N-methylimidazole were reacted to give 27.

Example 23

9-bromo-5,6-dihydrobenzo[f]imidazo[1,2-d][1,4]oxazepine-2-carboxylic acid 28

Ethyl 2-(4-bromo-2-fluorophenyl)-1-(2-hydroxyethyl)-1H-imidazole-4-carboxylate 27, potassium hydroxide and methyl tributylammonium hydrochloride were reacted at 65° C., cooled, and concentrated. The mixture was dissolved in ethanol and water to crystallize 28.

Example 24

9-bromo-N-(1-iminoethyl)-5,6-dihydrobenzo[f]imidazo[1,2-d][1,4]oxazepine-2-carboxamide 29

9-Bromo-5,6-dihydrobenzo[f]imidazo[1,2-d][1,4]oxazepine-2-carboxylic acid 28, triphenylphosphine, and acetamidine were reacted to give 29.

Example 25

9-bromo-2-(1-isopropyl-3-methyl-1H-1,2,4-triazol-5-yl)-5,6-dihydrobenzo[f]imidazo[1,2-d][1,4]oxazepine III 9-Bromo-N-(1-iminoethyl)-5,6-dihydrobenzo[f]imidazo[1,2-d][1,4]oxazepine-2-carboxamide 29 was reacted with isopropylhydrazine hydrochloride 4 in acetic acid to give III.

Example 26

2-(4-bromo-2-fluorophenyl)-1H-imidazole-4-carboxylic acid 30

3-Chloro-2-oxopropanoic acid and 4-bromo-2-fluorobenzimidamide hydrochloride 12 are reacted with base to give 2-(4-bromo-2-fluorophenyl)-1H-imidazole-4-carboxylic acid 30.

Alternatively, to a solution of ethyl 2-(4-bromo-2-fluorophenyl)-1H-imidazole-4-carboxylate 26 (1350 g, 4.3 mol) in THF (8.1 L, 6 vol) and H₂O (4 L, 3 vol) was added NaOH (520 g, 13 mol, 3 eq), and the reaction was stirred at 65° C. for 48 h till it completed (checked by LC-MS). Adjust the mixture with 2 M HCl to pH=5, and product was separated out as a yellow solid, filtered to give 2.2 kg wet cake, the wet cake was washed with H₂O (1.5 L), DCM (1.5 L×3), PE (1 L), and dried to afford 970 g pure 2-(4-bromo-2-fluorophenyl)-1H-imidazole-4-carboxylic acid 30 (Scheme 10).

Example 27

5-(2-(4-bromo-2-fluorophenyl)-1H-imidazol-4-yl)-1-isopropyl-3-methyl-1H-1,2,4-triazole V Reaction of 30 with N'-isopropylacetohydrazonamide 6 and coupling reagent HBTU in DMF gives intermediate, 2-(4-bromo-2-fluorophenyl)-N-(1-(2-isopropylhydrazinyl)ethylidene)-1H-imidazole-4-carboxamide 31 which cyclizes upon heating to give V.

Example 28

Tert-butyl 2-hydroxyethylcarbamate gives tert-butyl 2-(5-bromo-2-cyanophenoxy)ethylcarbamate 32

Alkylation of 4-bromo-2-fluorobenzonitrile 11 with tert-butyl 2-hydroxyethylcarbamate gives 32.

Example 29

8-bromo-3,4-dihydrobenzo[f][1,4]oxazepin-5(2H)-imine 33

Cyclization of tert-butyl 2-hydroxyethylcarbamate gives tert-butyl 2-(5-bromo-2-cyanophenoxy)ethylcarbamate 32 under acidic conditions, such as hydrochloric acid in ethanol, gives 33.

Example 30

9-bromo-5,6-dihydrobenzo[f]imidazo[1,2-d][1,4]oxazepine-2-carboxylic acid 28

Reaction of 3-bromo-2-oxopropanoic acid and 8-bromo-3,4-dihydrobenzo[f][1,4]oxazepin-5(2H)-imine 33 gives 28 (CAS Reg. No. 1282516-74-8).

Example 31

9-bromo-2-(1-isopropyl-3-methyl-1H-1,2,4-triazol-5-yl)-5,6-dihydrobenzo[f]imidazo[1,2-d][1,4]oxazepine III Coupling of 28 with N'-isopropylacetohydrazonamide 6 and coupling reagent HBTU in DMF gives intermediate, 9-bromo-N-(1-(2-isopropylhydrazinyl)ethylidene)-5,6-dihydrobenzo[f]imidazo[1,2-d][1,4]oxazepine-2-carboxamide 34, which forms III upon heating.

Example 32

Methyl 4-bromo-2-fluorobenzimidate 35

Reaction of 4-bromo-2-fluorobenzonitrile 11 with sodium methoxide in methanol gives 35.

Example 33

8-bromo-3,4-dihydrobenzo[f][1,4]oxazepin-5(2H)-imine 33

Alkylation of methyl 4-bromo-2-fluorobenzimidate 35 with 2-aminoethanol gives 4-bromo-2-fluoro-N-(2-hydroxyethyl)benzimidamide 36, followed by cyclization to 33 (Scheme 13).

Alternatively, reaction of 11 with 2-aminoethanol and potassium tert-butoxide displaces fluorine to give 2-(2-aminoethoxy)-4-bromobenzonitrile hydrochloride 37. Ring closure of 37 with trimethylaluminum gave 33 (Scheme 14). A solution of 11 (10 g, 50 mmol) and 2-aminoethanol (3.1 mL, 50.8 mmol) in 2-methyltetrahydrofuran (80 mL) was cooled to 0° C. and a solution of 1M potassium tert-butoxide in tetrahydrofuran (55 mL, 55 mmol) was slowly added while maintaining the solution temperature below 5° C. The reaction was stirred at 0° C. for 30 min until judged complete by HPLC at which point it was warmed to 25° C. A solution of 0.5M HCl in isopropanol (100 mL, 50 mmol) was added and the desired HCl salt 3 crystallized directly from the solution. The solid was collected by filtration and dried under vacuum with a nitrogen bleed to give 2-(2-aminoethoxy)-4-bromobenzonitrile hydrochloride 37 as a white solid. (12.1 g, 87% yield).

To a flask was charged 37 (9.00 g, 32.4 mmol) and toluene (90.0 ml). The suspension was cooled to 0° C. and was added trimethylaluminum (1.8 equiv., 58.4 mmol, 2M in toluene) drop-wise over 30 minutes. The suspension was then stirred at room temperature for 1 h and then warmed to 100° C. After 5 h, the solution was cooled to 0° C. and quenched with aqueous NaOH (2N, 90.0 ml). The suspension was extracted with EtOAc (4×90 ml) and the combined extracts were dried over then filtered through Celite®. The solution was concentrated and the residue triturated with EtOAc to afford 8-bromo-3,4-dihydrobenzo[f][1,4]oxazepin-5(2H)-imine 33 (6.26 g, 26.0 mmol, 80% yield) as white crystalline solid.

Example 34

4-chloro-2-fluoro-N-hydroxybenzimidamide 39

To a solution of 4-chloro-2-fluorobenzonitrile 38 (400 g, 2.58 mol, 1.0 eq), hydroxylamine hydrochloride (448 g, 6.45 mol, 2.5 eq) in MeOH (1 L, 2.5 vol) was added Et3N (313 g, 3.1 mol, 1.2 eq), then the mixture was stirred at 60° C. for 40 min and checked by HPLC (no nitrile remaining) Reaction was then quenched by $H_2O$ (10 L), and lots of off-white solid was separated out, and then filtered, the filter cake was washed with water (10 L×2) and 378 g 4-chloro-2-fluoro-N-hydroxybenzimidamide 39 was obtained with 93% purity (Scheme 15).

Example 35

Ethyl 3-(4-chloro-2-fluorobenzimidamidooxy)acrylate 40

To a solution of 4-chloro-2-fluoro-N-hydroxybenzimidamide 39 (378 g, 2 mol, 1.0 eq) and Amberlyst® A21 (20 wt %, 75.6 g) in toluene PhMe (5.6 L, 15 vol) was added ethyl propiolate (275 g, 2.8 mol, 1.4 eq) at 30° C. The reaction was stirred at 30° C. overnight and checked by LC-MS. Reaction was then filtered and the filtrate was concentrated under vacuum, and 550 g ethyl 3-(4-chloro-2-fluorobenzimidamidooxy)acrylate 40 was obtained as a yellow oil with 83% LC purity (Scheme 15).

Example 36

Ethyl 2-(4-chloro-2-fluorophenyl)-1H-imidazole-4-carboxylate 41

A solution of ethyl 3-(4-chloro-2-fluorobenzimidamidooxy)acrylate 40 (550 g, 1.9 mol, 1.0 eq, 83% LC purity) in diphenyl oxide (1.65 L, 3 vol) was stirred at 190° C. under N2 for 1 h and checked by LC-MS (no 40 remaining) Cooled the mixture to rt and PE (10 L) was added dropwise. The mixture was stirred at rt for 20 min, and filtered to give 400 g wet cake, after purified by chromatography on silica gel (PE/EA=1/5) to get 175 g pure ethyl 2-(4-chloro-2-fluorophenyl)-1H-imidazole-4-carboxylate 41 with 98% LC purity (Scheme 15).

Example 37

2-(4-chloro-2-fluorophenyl)-1H-imidazole-4-carboxylic acid 42

To a solution of ethyl 2-(4-chloro-2-fluorophenyl)-1H-imidazole-4-carboxylate 41 (175 g, 4.3 mol) in THF (1 L, 6 vol) and $H_2O$ (500 mL, 3 vol) was added NaOH (78 g, 1.95 mol, 3.0 eq), and the reaction was stirred at 65° C. for 48 h till it completed (checked by LC-MS). Adjust the mixture with 2 N HCl to pH=5, and product was separated out as a yellow solid, filtered to give 210 g wet cake, the wet cake was washed with $H_2O$ (300 mL), DCM (3×300 mL), PE (500 mL), and dried to afford 110 g pure 2-(4-chloro-2-fluorophenyl)-1H-imidazole-4-carboxylic acid 42 (CAS Reg. No. 1260649-87-3) (Scheme 15). 1H NMR (DMSO d6) δ: 12.8 (br s), 8.0, 7.9 (br s), 7.46, 7.4 (m), Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

What is claimed is:

1. A process for preparing (2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide I, having the structure:

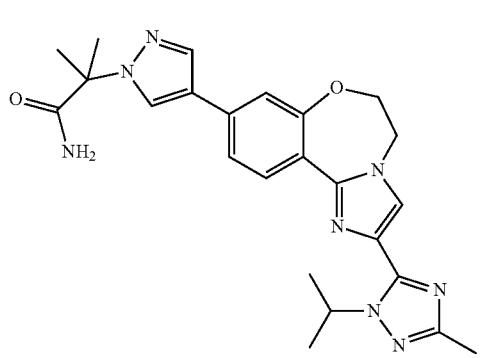

and stereoisomers, geometric isomers, tautomers, and pharmaceutically acceptable salts thereof, comprising:

(a) reacting IV and 4,4,4',4',5,5,5',5'-octamethyl-2,2'-bi(1,3,2-dioxaborolane) to form 22

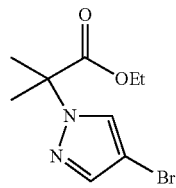
IV

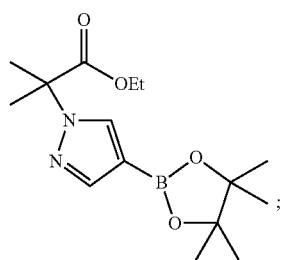
22

(b) reacting 22, a palladium catalyst, and III to form 23

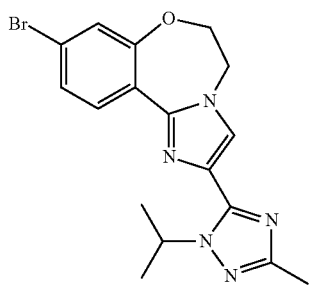
III

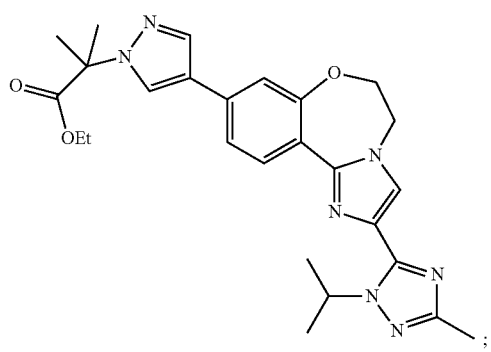
23

(c) reacting 23 with an aqueous basic reagent to form II

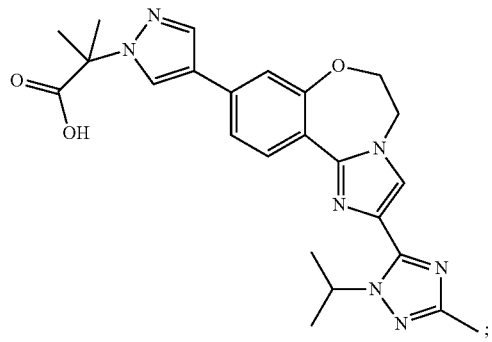
II and
(d) reacting II with an acyl activating reagent, followed by ammonia to give I.

2. The process of claim 1 wherein IV is prepared by reacting 17:

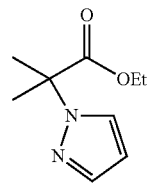
17 with a brominating reagent.

3. The process of claim 1 wherein the palladium catalyst is selected from PdCl$_2$(PPh$_3$)$_2$, Pd(t-Bu)$_3$, PdCl$_2$ dppf CH$_2$Cl$_2$, Pd(PPh$_3$)$_4$, Pd(OAc)/PPh$_3$, Cl$_2$Pd[(Pet$_3$)]$_2$, Pd(DIPHOS)$_2$, Cl$_2$Pd(Bipy), [PdCl(Ph$_2$PCH$_2$PPh$_2$)]$_2$, Cl$_2$Pd[P(o-tol)$_3$]$_2$, Pd$_2$(dba)$_3$/P(o-tol)$_3$, Pd$_2$(dba)/P(furyl)$_3$, Cl$_2$Pd[P(furyl)$_3$]$_2$, Cl$_2$Pd(PMePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, Cl$_2$Pd[P(4-COOH-Ph)(Ph)$_2$]$_2$, and encapsulated catalysts Pd EnCat™ 30, Pd EnCat™ TPP30, and Pd(II)EnCat™ BINAP30.

4. The process of claim 1 wherein palladium is removed from I with a solid adsorbent palladium scavenger.

5. The process of claim 4 wherein the solid adsorbent palladium scavenger is selected from silica gel, controlled-pore glass, and low crosslinked polystyrene.

6. The process of claim 1 wherein III is prepared by:
(a) reacting V with a 2-hydroxyethylation reagent to form 14

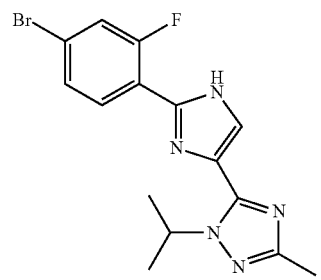
V

-continued

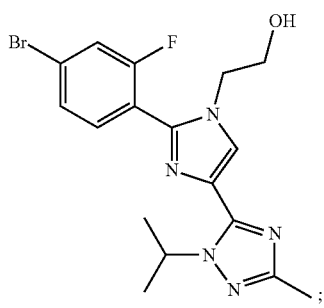
14 and (b) reacting 14 with an aqueous basic reagent to form V.

7. The process of claim 1 wherein III is prepared by:
(a) reacting 28 with acetamidine to form 29

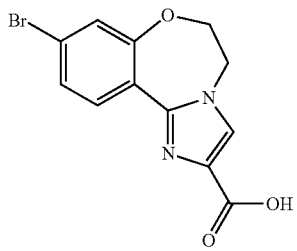
28

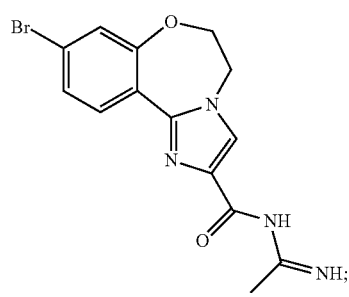
29 and (b) reacting 29 with isopropyl hydrazine and an acidic reagent to form III.

8. The process of claim 1 wherein III is prepared by reacting 28 with N'-isopropylacetohydrazonamide 6 to form III

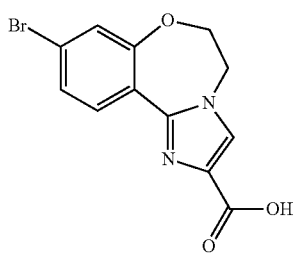
28

-continued

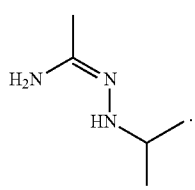
6

9. The process of claim 7 wherein 28 is prepared by:
(a) reacting 11 with hydroxylamine to form 24

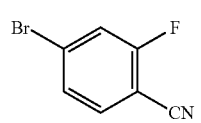
11

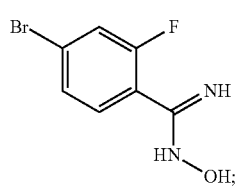
24

(b) reacting 24 with ethyl propiolate to form 25

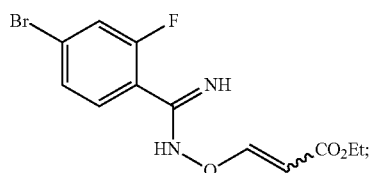
25

(c) heating 25 to form 26

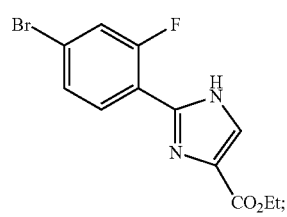
26

(d) reacting 26 with a 2-hydroxyethylation reagent to form 27

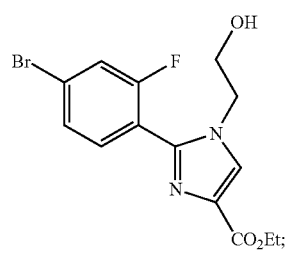
27 and (e) reacting 27 with an aqueous basic reagent to form 28.

10. A compound selected from the structures:
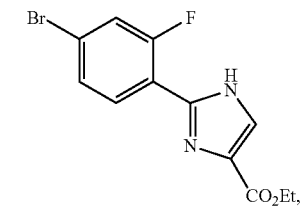
26
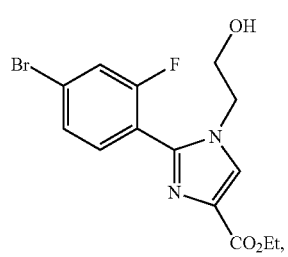
27
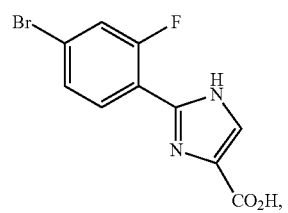
30
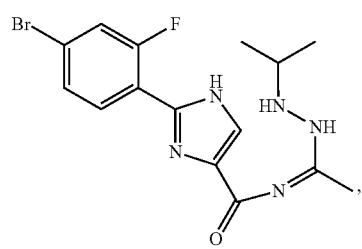
31
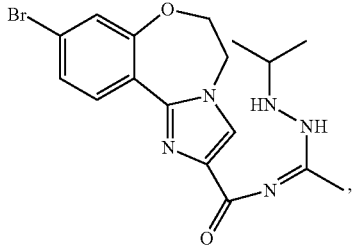
34
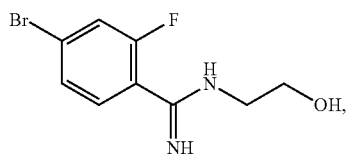
36
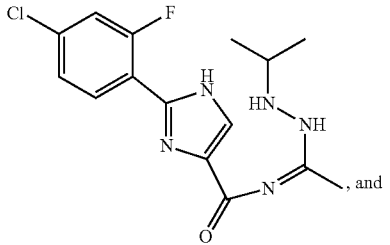
43
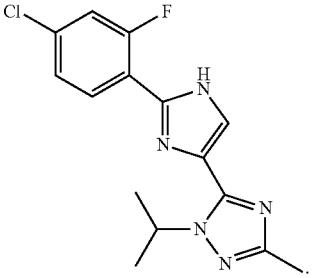
44
* * * * *